United States Patent  
Abe et al.

(10) Patent No.: US 12,359,254 B2  
(45) Date of Patent: Jul. 15, 2025

(54) PRIMER, DEVICE FOR PRODUCING DOUBLE-STRANDED DNA USING PRIMER, AND METHOD FOR PRODUCING DOUBLE-STRANDED DNA USING PRIMER

(71) Applicant: Japan Science and Technology Agency, Kawaguchi (JP)

(72) Inventors: Hiroshi Abe, Nagoya (JP); Naoko Abe, Nagoya (JP); Kosuke Nakamoto, Nagoya (JP); Hiroki Murase, Nagoya (JP); Yasuaki Kimura, Nagoya (JP)

(73) Assignee: Japan Science and Technology Agency, Kawaguchi (JP)

( * ) Notice: Subject to any disclaimer, the term of this patent is extended or adjusted under 35 U.S.C. 154(b) by 743 days.

(21) Appl. No.: 17/631,418

(22) PCT Filed: Jul. 31, 2020

(86) PCT No.: PCT/JP2020/029441  
§ 371 (c)(1),  
(2) Date: Jan. 28, 2022

(87) PCT Pub. No.: WO2021/020561  
PCT Pub. Date: Feb. 4, 2021

(65) Prior Publication Data  
US 2022/0290232 A1  Sep. 15, 2022

(30) Foreign Application Priority Data  
Jul. 31, 2019 (JP) ................. 2019-140851

(51) Int. Cl.  
*C12Q 1/68* (2018.01)  
*C12Q 1/6876* (2018.01)

(52) U.S. Cl.  
CPC ................. *C12Q 1/6876* (2013.01)

(58) Field of Classification Search  
CPC ....... C12Q 1/6876; C12P 19/34; C07H 19/10; C07H 19/20  
See application file for complete search history.

(56) References Cited

U.S. PATENT DOCUMENTS  
2011/0009607 A1  1/2011  Komiyama et al.

FOREIGN PATENT DOCUMENTS  
EP  2270142 A1  1/2011  
WO  2009113709 A1  9/2009  
(Continued)

OTHER PUBLICATIONS  
Dantzman et al., "Reactivity of 2'-Thio Nucleotide Analog", J. Am. Chem. Soc., 1996, pp. 11715-11719, vol. 118, American Chemical Society.  
(Continued)

*Primary Examiner* — Jezia Riley  
(74) *Attorney, Agent, or Firm* — The Webb Law Firm

(57) ABSTRACT

(Continued)

where $A_1$ represents —S—, —S—S—, or —Se—, B represents a base, and $R_1$ represents a decomposable protecting group, and the symbol * represents a bond to a sugar of an adjacent nucleotide. A device for producing double-stranded DNA includes: a forward primer and a reverse primer, having a structure represented by formula (1); a PCR device for forming double-stranded DNA with 3'-recessed ends by performing multiple cycles of PCR by using a template DNA as a template; Klenow fragment for making the 3' ends blunt; and a photoirradiation unit for deprotecting $R_1$ and forming a sticky end with a 3'-protruding end.

13 Claims, 4 Drawing Sheets

Specification includes a Sequence Listing.

(56) References Cited

FOREIGN PATENT DOCUMENTS

| | | |
|---|---|---|
| WO | 2015125845 A1 | 8/2015 |
| WO | 2019172394 A1 | 9/2019 |

OTHER PUBLICATIONS

Hamm et al., "Synthesis and Characterization of Oligonucleotides Containing 2'-S,3'-O-Cyclic Phosphorothiolate Termini", J. Org. Chem., 1999, pp. 5700-5704, vol. 64, American Chemical Society.

Murase et al., "Development of new DNA assembly method for genome synthesis", 2020, pp. 1-2, The Chemical Society of Japan, English-language Abstract.

Maier et al. "Nucleotides—New Types of Fluorescence Labeling of 2'-Deoxycytidine", Helvetica Chemica, 2009, pp. 2722-2736, vol. 92.

Ozaki et al., Post-synthetic functionalization of oligodeoyxribonucleotides at the 2'-position, Tetrahedron Letters, 2001, pp. 677-680, vol. 42, Elsevier Science, Ltd.

Saneyoshi et al., "Synthesis and Characterization of Cell-Permeable Oligonucleotides Bearing Reduction-Activated Protecting Groups on the Internucleotide Linkages", Bioconjugate Chemistry, 2016, pp. 2149-2156, vol. 27, ACS Publications.

Wu et al., "Synthesis of Site-Specifically Phosphate-Caged siRNAs and Evaluation of Their RNAi Activity and Stability", Chem. Eur. J., 2014, pp. 12114-12122, vol. 20, Wiley-VCH Verlag GmbH & Co. KGaA, Weinheim.

Höbartner et al., "Chemical Synthesis of Selenium-Modified Oligoribonucleotides and Their Enzymatic Ligation Leading to an U6 SnRNA Stem-Loop Segment", Journal of the American Chemical Society, Jan. 9, 2004, pp. 1141-1149, vol. 126.

Jud et al., "Expanding the Scope of 2'-SCF3 Modified RNA", Chem. Eur. J., 2015, pp. 10400-10407, vol. 21.

[FIG. 1]
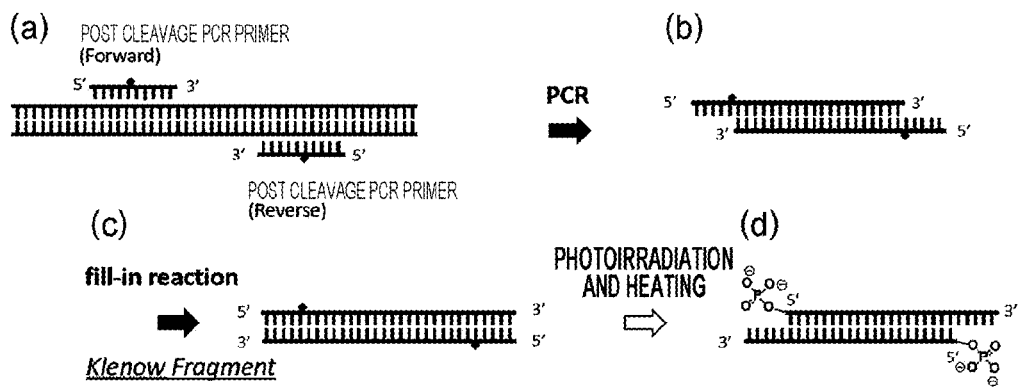
[FIG. 2]
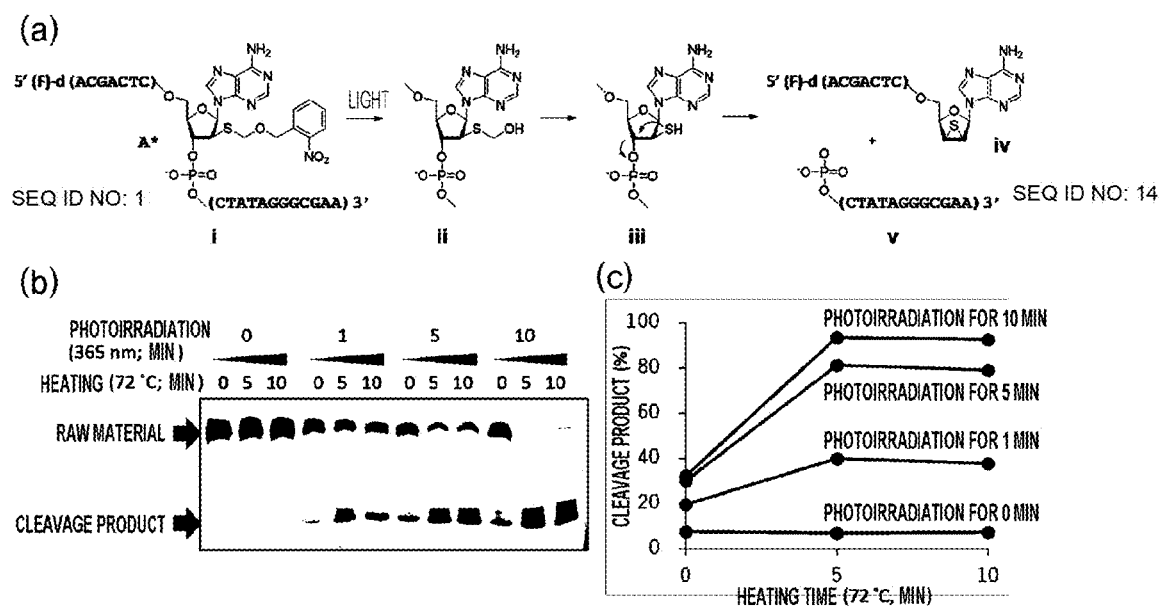

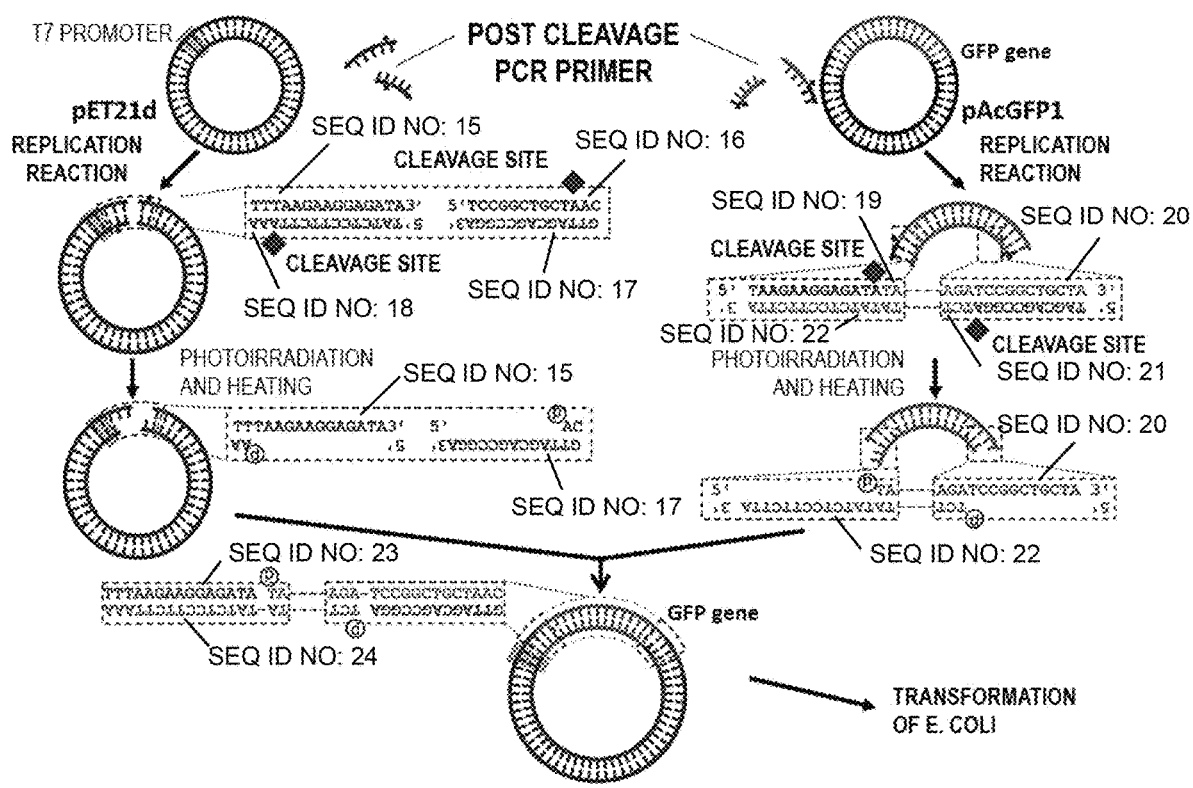
[FIG. 3]

[FIG. 4]
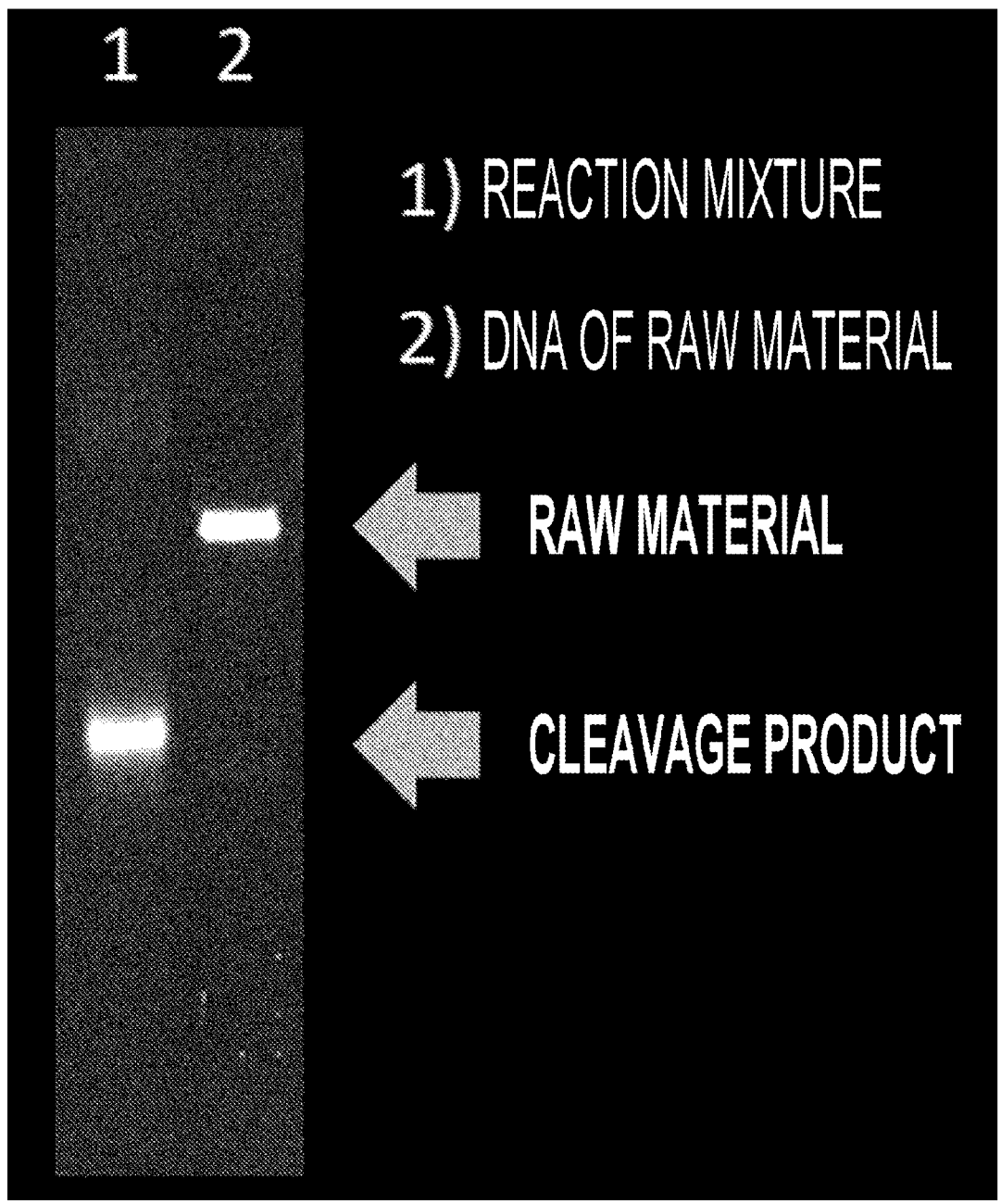

[FIG. 5]
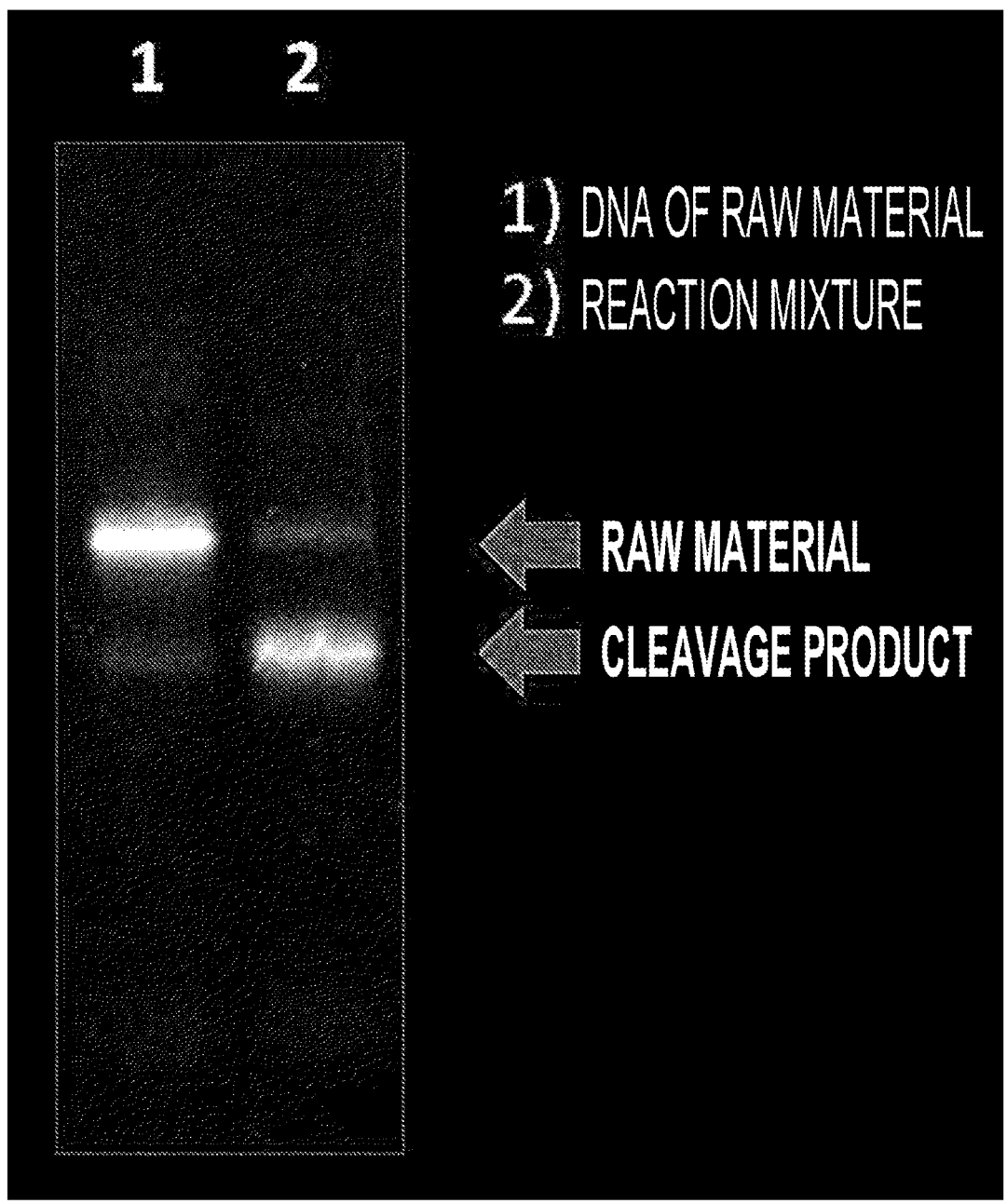

```
                           SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: 5' fluorescein-d oligonucleotide
<220> FEATURE:
<221> NAME/KEY: misc_feature
<222> LOCATION: (1)..(1)
<223> OTHER INFORMATION: 5' fluorescein modified
<220> FEATURE:
<221> NAME/KEY: misc_feature
<222> LOCATION: (8)..(8)
<223> OTHER INFORMATION: n is photocleavage analog A*

<400> SEQUENCE: 1
acgactcnct atagggcgaa                                              20

<210> SEQ ID NO 2
<211> LENGTH: 28
<212> TYPE: DNA
<213> ORGANISM: Artificial Sequence
<220> FEATURE:
<223> OTHER INFORMATION: pET21d Forward
<220> FEATURE:
<221> NAME/KEY: misc_feature
<222> LOCATION: (11)..(11)
<223> OTHER INFORMATION: n is a, c, g, or t

<400> SEQUENCE: 2
tccggctgct nacaaagccc gaaaggaa                                     28

<210> SEQ ID NO 3
<211> LENGTH: 33
<212> TYPE: DNA
<213> ORGANISM: Artificial Sequence
<220> FEATURE:
<223> OTHER INFORMATION: pET21d Reverse
<220> FEATURE:
<221> NAME/KEY: misc_feature
<222> LOCATION: (13)..(13)
<223> OTHER INFORMATION: n is photocleavage analog A*

<400> SEQUENCE: 3
tatctccttc ttnaagttaa acaaaattat ttc                               33

<210> SEQ ID NO 4
<211> LENGTH: 35
<212> TYPE: DNA
<213> ORGANISM: Artificial Sequence
<220> FEATURE:
<223> OTHER INFORMATION: pAcGFP1 Forward
<220> FEATURE:
<221> NAME/KEY: misc_feature
<222> LOCATION: (13)..(13)
<223> OTHER INFORMATION: n is photocleavage analog A*

<400> SEQUENCE: 4
taagaaggag atntaccatg gtgagcaagg gcgcc                             35
```

```
<210> SEQ ID NO 5
<211> LENGTH: 34
<212> TYPE: DNA
<213> ORGANISM: Artificial Sequence
<220> FEATURE:
<223> OTHER INFORMATION: pAcGFP1 Reverse
<220> FEATURE:
<221> NAME/KEY: misc_feature
<222> LOCATION: (11)..(11)
<223> OTHER INFORMATION: n is photocleavage analog A*

<400> SEQUENCE: 5
tagcagccgg ntctcacttg tacagctcat ccat                            34

<210> SEQ ID NO 6
<211> LENGTH: 20
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (1)..(1)
<223> OTHER INFORMATION: 5' is 6-FAM amidite modified
<220> FEATURE:
<221> NAME/KEY: misc_feature
<222> LOCATION: (8)..(8)
<223> OTHER INFORMATION: n is photocleavage analog A*

<400> SEQUENCE: 6
acgactcnct atagggcgaa                                             20

<210> SEQ ID NO 7
<211> LENGTH: 20
<212> TYPE: DNA
<213> ORGANISM: Artificial Sequence
<220> FEATURE:
<223> OTHER INFORMATION: DNA Primer
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (1)..(1)
<223> OTHER INFORMATION: 5' is 6-FAM amidite modified
<220> FEATURE:
<221> NAME/KEY: misc_feature
<222> LOCATION: (8)..(8)
<223> OTHER INFORMATION: n is fluorine cleavage analog A**

<400> SEQUENCE: 7
acgactcnct atagggcgaa                                             20

<210> SEQ ID NO 8
<211> LENGTH: 26
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (9)..(9)
<223> OTHER INFORMATION: n is photocleavage analog A*

<400> SEQUENCE: 8
tcggtgctna caaagcccga aaggaa                                      26
```

<210> SEQ ID NO 9
<211> LENGTH: 33
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (13)..(13)
<223> OTHER INFORMATION: n is photocleavage analog A*

<400> SEQUENCE: 9
tatctccttc ttnaagttaa acaaaattat ttc                                33

<210> SEQ ID NO 10
<211> LENGTH: 35
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (13)..(13)
<223> OTHER INFORMATION: n is photocleavage analog A*

<400> SEQUENCE: 10
taagaaggag atntaccatg gtgagcaagg gcgcc                              35

<210> SEQ ID NO 11
<211> LENGTH: 35
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (12)..(12)
<223> OTHER INFORMATION: n is photocleavage analog A*

<400> SEQUENCE: 11
tagcagcccg gntctcactt gtacagctca tccat                              35

<210> SEQ ID NO 12
<211> LENGTH: 20
<212> TYPE: DNA
<213> ORGANISM: Artificial Sequence
<220> FEATURE:
<223> OTHER INFORMATION: 5' fluorescein-d oligonucelotide
<220> FEATURE:
<221> NAME/KEY: misc_feature
<222> LOCATION: (1)..(1)
<223> OTHER INFORMATION: 5' fluorescein modified
<220> FEATURE:
<221> NAME/KEY: misc_feature
<222> LOCATION: (8)..(8)
<223> OTHER INFORMATION: n is fluorine cleavage analog A**

<400> SEQUENCE: 12
acgactcnct atagggcgaa                                               20

<210> SEQ ID NO 13
<211> LENGTH: 32
<212> TYPE: DNA
<213> ORGANISM: Artificial Sequence
<220> FEATURE:
<223> OTHER INFORMATION: DNA oligomer
<220> FEATURE:
<221> NAME/KEY: misc_feature
<222> LOCATION: (8)..(8)
<223> OTHER INFORMATION: n is photocleavage analog A(Se)

```
<400> SEQUENCE: 13
acgactcnct atagggcgaa ttcgagctcg gt                                  32

<210> SEQ ID NO 14
<211> LENGTH: 12
<212> TYPE: DNA
<213> ORGANISM: Artificial Sequence
<220> FEATURE:
<223> OTHER INFORMATION: cleavage reaction product
<220> FEATURE:
<221> NAME/KEY: misc_feature
<222> LOCATION: (1)..(1)
<223> OTHER INFORMATION: 5' is monophosphate

<400> SEQUENCE: 14
ctatagggcg aa                                                       12

<210> SEQ ID NO 15
<211> LENGTH: 15
<212> TYPE: DNA
<213> ORGANISM: Artificial Sequence
<220> FEATURE:
<223> OTHER INFORMATION: partial sequence of pET21d forward

<400> SEQUENCE: 15
tttaagaagg agata                                                    15

<210> SEQ ID NO 16
<211> LENGTH: 13
<212> TYPE: DNA
<213> ORGANISM: Artificial Sequence
<220> FEATURE:
<223> OTHER INFORMATION: partial sequence of pET21d forward
<220> FEATURE:
<221> NAME/KEY: misc_feature
<222> LOCATION: (11)..(11)
<223> OTHER INFORMATION: n is photocleavage analog A*

<400> SEQUENCE: 16
tccggctgct nac                                                      13

<210> SEQ ID NO 17
<211> LENGTH: 13
<212> TYPE: DNA
<213> ORGANISM: Artificial Sequence
<220> FEATURE:
<223> OTHER INFORMATION: partial sequence of pET21d reverse

<400> SEQUENCE: 17
gttagcagcc gga                                                      13

<210> SEQ ID NO 18
<211> LENGTH: 15
<212> TYPE: DNA
<213> ORGANISM: Artificial Sequence
<220> FEATURE:
<223> OTHER INFORMATION: partial sequence of pET21d reverse
<220> FEATURE:
<221> NAME/KEY: misc_feature
<222> LOCATION: (13)..(13)
<223> OTHER INFORMATION: n is photocleavage analog A*

<400> SEQUENCE: 18
tatctccttc ttnaa                                                    15

<210> SEQ ID NO 19
```

```
<211> LENGTH: 15
<212> TYPE: DNA
<213> ORGANISM: Artificial Sequence
<220> FEATURE:
<223> OTHER INFORMATION: partial sequence of pAcGFp1 forward
<220> FEATURE:
<221> NAME/KEY: misc_feature
<222> LOCATION: (13)..(13)
<223> OTHER INFORMATION: n is photocleavage analog A*

<400> SEQUENCE: 19
taagaaggag atnta                                              15

<210> SEQ ID NO 20
<211> LENGTH: 14
<212> TYPE: DNA
<213> ORGANISM: Artificial Sequence
<220> FEATURE:
<223> OTHER INFORMATION: partial sequence of pAcGFP1 forward

<400> SEQUENCE: 20
agatccggct gcta                                               14

<210> SEQ ID NO 21
<211> LENGTH: 14
<212> TYPE: DNA
<213> ORGANISM: Artificial Sequence
<220> FEATURE:
<223> OTHER INFORMATION: partial sequence of pAcGFP1 reverse
<220> FEATURE:
<221> NAME/KEY: misc_feature
<222> LOCATION: (11)..(11)
<223> OTHER INFORMATION: n is a photocleavage analog A*

<400> SEQUENCE: 21
tagcagccgg ntct                                               14

<210> SEQ ID NO 22
<211> LENGTH: 15
<212> TYPE: DNA
<213> ORGANISM: Artificial Sequence
<220> FEATURE:
<223> OTHER INFORMATION: partial sequence of pAcGFP1 reverse

<400> SEQUENCE: 22
tatatctcct tctta                                              15

<210> SEQ ID NO 23
<211> LENGTH: 33
<212> TYPE: DNA
<213> ORGANISM: Artificial Sequence
<220> FEATURE:
<223> OTHER INFORMATION: partial sequence of a plasmid DNA_Fw obtained
      by ligation of an insert fragment and a vector fragment

<400> SEQUENCE: 23
tttaagaagg agatataaga tccggctgct aac                          33
```

```
<210> SEQ ID NO 24
<211> LENGTH: 33
<212> TYPE: DNA
<213> ORGANISM: Artificial Sequence
<220> FEATURE:
<223> OTHER INFORMATION: partial sequence of a plasmid DNA_Rev obtained
      by ligation of an insert fragment and a vector fragment

<400> SEQUENCE: 24
gttagcagcc ggatcttata tctccttctt aaa                              33
```

PRIMER, DEVICE FOR PRODUCING DOUBLE-STRANDED DNA USING PRIMER, AND METHOD FOR PRODUCING DOUBLE-STRANDED DNA USING PRIMER

CROSS-REFERENCE TO RELATED APPLICATIONS

This application is the United States national phase of International Application No. PCT/JP2020/029441 filed Jul. 31, 2020, and claims priority to Japanese Patent Application No. 2019-140851 filed Jul. 31, 2019, the disclosures of which are hereby incorporated by reference in their entirety.

REFERENCE TO A SEQUENCE LISTING SUBMITTED VIA PATENT CENTER

The Sequence Listing associated with this application is filed in electronic format via Patent Center and is hereby incorporated by reference into the specification in its entirety. The name of the text file containing the Sequence Listing is 02714-2200305_ST25.txt. The size of the text file is 7,373 bytes, and the text file was created on Dec. 13, 2024.

BACKGROUND OF THE INVENTION

Field of the Invention

The present invention relates to a primer, a device for producing double-stranded DNA using the primer, and a method for producing double-stranded DNA using the primer.

Description of Related Art

In the field of molecular biology or the like, a vector obtained by incorporating a target DNA into a host has been used in order to perform gene recombination, transformation, or the like. In general, the target DNA is amplified for use by polymerase chain reaction (PCR) in a case where the amount is small. In the PCR, by using a template DNA containing a target DNA sequence and using a primer that binds complementarily to the template DNA, the template DNA is amplified by repeating a cycle of thermal denaturation and annealing multiple times.

An amplification product obtained by amplifying a template DNA by PCR has blunt ends originally, and it is necessary to perform a treatment for binding (ligating) the amplification product to a host DNA such as a plasmid DNA. In general, in such a treatment, a restriction enzyme that cleaves a specific sequence is used, but in this method, there is a problem that the versatility is poor because the DNA that can be bound depends on the sequence at a cleavage site of the restriction enzyme.

As the method in which any restriction enzyme is not used, there is a technique for constructing a vector by forming the 3' end and 5' end of an amplification product as sticky ends (also referred to as "cohesive ends", "protruding ends" or the like), forming sticky ends also on the host side in a similar way, and ligating both of the ends. For example, as such a technique, Gibson assembly method, In-Fusion method, SLiCE method, or the like has been known in recent years. In any case of these methods, the end of a double-stranded DNA fragment is provided with a homologous sequence of around 15 bp, and the strand on one side in the double strand is digested with exonuclease activity to generate a sticky end, and then the sticky end is ligated. Note that in the Gibson assembly method, the ends are ligated by using a Taq DNA ligase in vitro, and in the In-Fusion method, the ends are ligated by using a repair system in *E. coli*.

In these methods, since an exonuclease that is an enzyme is used, a significant cost is required, and further, the site specificity may be inferior depending on the reaction conditions and the like, and it is difficult to quantitatively form sticky ends, and thus there has been a problem that the efficiency of ligation reaction is low. For this reason, a seamless cloning method in which an enzyme is not used has been demanded.

Accordingly, a method for preparing DNA having sticky ends by a chemical technique has been developed, and as the primer for PCR for the method, a primer disclosed in WO 2009/113709 is known. In the primer of this literature, a base corresponding to the 3' end in the nucleotide sequence of a non-complementary DNA part is modified with a protecting group. This protecting group has a function of terminating the progress of DNA replication by DNA polymerase, and can be desorbed from the base to be modified by photoirradiation treatment, alkali treatment, or the like. In addition, in this literature, a protecting group (substituent) is introduced into the base of a primer by using a substituent introduction agent for introducing the protecting group into a biomolecule.

CITATION LIST

Patent Literature

Patent Literature 1: WO 2009/113709 (claim 1, claim 2, and the like)

SUMMARY OF THE INVENTION

Technical Problem

In WO 2009/113709, the progress of DNA replication is terminated in the moiety of a protecting group, but the single-stranded DNA is not cleaved at a specific site to generate a sticky end, and thus the site specificity is low. Further, for example, in DNA, there are four kinds of bases of adenine, guanine, cytosine, and thymine, and in WO 2009/113709, since a protecting group is introduced into a base, it is necessary to introduce the protecting group by a method depending on the kind of the base, and thus labor and cost are required to produce a primer.

An object of the present invention is to provide a primer that can specifically cleave a single strand at a specific site and further can be produced at a low cost. Further, another object of the present invention is to provide a device for producing double-stranded DNA having sticky ends and a method for producing double-stranded DNA, which each use the primer described above.

The present inventors have conducted the intensive studies to solve the problem described above. As a result, the present inventors have developed a primer in which a decomposable protecting group is introduced into a sugar moiety of the nucleoside via a specific linker. Further, the present inventors have found that by decomposing the protecting group and cleaving the single strand at the nucleoside moiety, double-stranded DNA having sticky ends can be prepared, and thus have completed the present invention.

That is, the present invention is a primer used for amplifying a nucleic acid, having a structure represented by the following formula (1):

[Chemical formula 1]

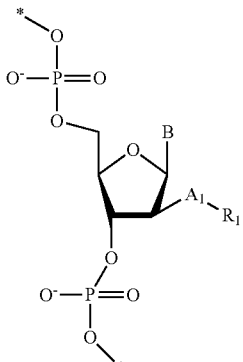

(1)

where, $A_1$ represents —S—, —S—S—, or —Se—, B represents a base, $R_1$ represents a decomposable protecting group, and the symbol * represents a bond to a sugar of an adjacent nucleotide.

In this case, it is preferable that the $R_1$ is a photodecomposable protecting group represented by the following formula (2A):

[Chemical formula 2]

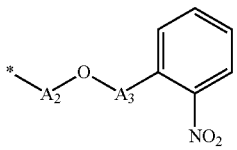

(2A)

where, $A_2$ represents an alkylene group having 1 to 3 carbon atoms, $A_3$ represents an alkylene group having 1 to 3 carbon atoms, and the symbol * represents a bond to $A_1$.

Further, it is preferable that the $R_1$ is a 2-nitrobenzyloxymethyl group represented by the following formula (3A):

[Chemical formula 3]

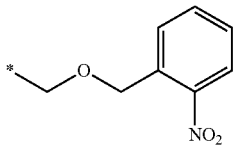

(3A)

Alternatively, it is preferable that the $R_1$ is a fluoride decomposable protecting group represented by the following formula (2B):

[Chemical formula 4]

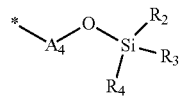

(2B)

where, $A_4$ represents an alkylene group having 1 to 3 carbon atoms, $R_2$ to $R_4$ each represent a straight or branched alkyl group having 1 to 4 carbon atoms, the $R_2$ to $R_4$ may be the same as or different from each other, and the symbol * represents a bond to $A_1$.

In this case, it is preferable that the $R_1$ is a triisopropylsilyloxymethyl group represented by the following formula (3B):

[Chemical formula 5]

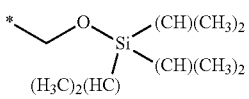

(3B)

Further, the present invention is a device for producing double-stranded DNA having sticky ends by using the primer described in any one of the above items, including: a forward primer being complementary to a part of a sequence of an antisense strand of a template DNA to be used as a template and having a structure represented by the formula (1); a reverse primer being complementary to a part of a sequence of a sense strand of the template DNA and having a structure represented by the formula (1); an amplification unit for performing multiple cycles of polymerase chain reaction (PCR) by using the template DNA as a template to form a forward-side extended chain being the forward primer extended and a reverse-side extended chain being the reverse primer extended, and for annealing the forward-side extended chain and the reverse-side extended chain to form double-stranded DNA with 3'-recessed ends; a blunting unit for making the 3' ends of the double-stranded DNA blunt by Klenow fragment; and a deprotection cleavage unit for deprotecting the $R_1$, and cleaving DNA at a structural part of the formula (1) to form a sticky end with a 3'-protruding end.

Furthermore, the present invention is a method for producing double-stranded DNA having sticky ends by using the primer described in any one of the above items, including: a preparation step of preparing a forward primer being complementary to a part of a sequence of an antisense strand of a template DNA to be used as a template and having a structure represented by the formula (1), and a reverse primer being complementary to a part of a sequence of a sense strand of the template DNA and having a structure represented by the formula (1); an amplification step of performing multiple cycles of polymerase chain reaction (PCR) by using the template DNA as a template to form a forward-side extended chain being the forward primer extended and a reverse-side extended chain being the reverse primer extended, and of annealing the forward-side extended chain and the reverse-side extended chain to form double-stranded DNA with 3'-recessed ends; a blunting step of making the 3' ends of the double-stranded DNA blunt by Klenow fragment; and a deprotection cleavage step of deprotecting the $R_1$, and cleaving DNA at a structural part of the formula (1) to form a sticky end with a 3'-protruding end.

In this case, it is preferable that the $R_1$ is a photodecomposable protecting group represented by the formula (2A) and is deprotected by photoirradiation in the deprotection cleavage step.

Alternatively, it is preferable that the $R_1$ is a fluoride decomposable protecting group represented by the formula (2B), and is deprotected by a fluoride in the deprotection cleavage step.

According to the present invention, a primer that can specifically cleave a single strand at a specific site and further can be produced at a low cost can be provided. Further, according to the present invention, a device for producing double-stranded DNA having sticky ends and a method for producing double-stranded DNA, which each use the primer described above, can be provided.

BRIEF DESCRIPTION OF THE DRAWINGS

FIG. 1 is a schematic diagram showing a method and a device, for producing double-stranded DNA having sticky ends.

FIG. 2 is a diagram showing the experiment of cleavage reaction of an oligonucleotide containing a photocleavage analog.

FIG. 3 is a diagram showing the experiment of cloning reaction utilizing the sticky end formation by photocleavage reaction.

FIG. 4 is a diagram showing the experimental results of cleavage reaction of an oligonucleotide containing a photocleavage analog.

FIG. 5 is a diagram showing the experimental results of cleavage reaction of an oligonucleotide containing a fluorine cleavage analog.

DESCRIPTION OF THE INVENTION

1. Primer

Hereinafter, the primer according to the present invention will be described. The primer according to the present invention is a primer used for amplifying a nucleic acid, and has a structure represented by the following formula (1):

[Chemical formula 6]

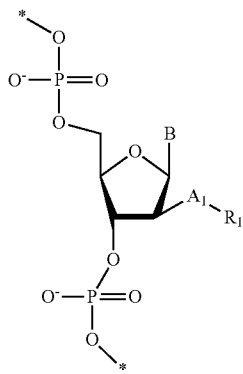

(1)

where, $A_1$ represents —S—, —S—S—, or —Se—, B represents a base, $R_1$ represents a decomposable protecting group, and the symbol * represents a bond to an adjacent nucleotide. In this regard, as to the bonds each represented by the symbol *, the bond on the 3'-end side of the formula (1) bonds to the 5' carbon of a sugar of an adjacent nucleotide on the 3'-end side, and the bond on the 5'-end side bonds to the 3' carbon of a sugar of an adjacent nucleotide on the 5'-end side.

The B represents a base, and is specifically selected from adenine, guanine, cytosine, and thymine in a case of a DNA primer, and is selected from adenine, guanine, cytosine, and uracil in a case of a RNA primer.

The decomposable protecting group of $R_1$ means a protecting group (substituent) that is decomposed by some kind of treatment. Examples of the treatment referred to herein include photoirradiation treatment, reduction treatment, alkali treatment, acid treatment, oxidation treatment, desilylation treatment, heat treatment, esterase treatment, and phosphatase treatment.

(1) Photodecomposable Protecting Group

In a case of photoirradiation treatment, it is preferable that $R_1$ is a photodecomposable protecting group represented by the following formula (2A):

[Chemical formula 7]

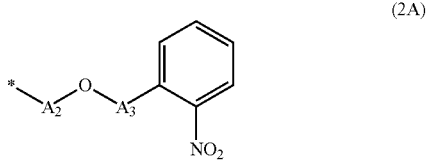

(2A)

where, $A_2$ represents an alkylene group having 1 to 3 carbon atoms, $A_3$ represents an alkylene group having 1 to 3 carbon atoms, and the symbol * represents a bond to $A_1$.

Examples of the alkylene group having 1 to 3 carbon atoms include a methylene group, an ethylene group, and a propylene group.

In particular, it is suitable that the $R_1$ is a 2-nitrobenzyloxymethyl group represented by the following formula (3A).

[Chemical formula 8]

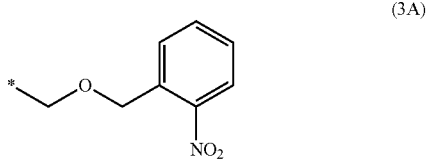

(3A)

(2) Fluoride Decomposable Protecting Group (Silyl-Based Protecting Group)

In a case of reduction treatment, it is preferable that $R_1$ is a fluoride decomposable protecting group (silyl-based protecting group) represented by the following formula (2B):

[Chemical formula 9]

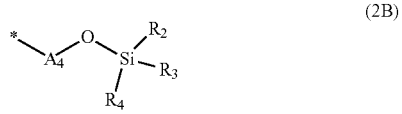

(2B)

where, $A_4$ represents an alkylene group having 1 to 3 carbon atoms, $R_2$ to $R_4$ each represent a straight or branched alkyl group having 1 to 4 carbon atoms, the $R_2$ to $R_4$ may be the same as or different from each other, and the symbol * represents a bond to $A_1$.

Examples of the straight or branched alkyl group having 1 to 4 carbon atoms include a methyl group, an ethyl group, a n-propyl group, an isopropyl group, a n-butyl group, a sec-butyl group, an isobutyl group, and a tert-butyl group.

In particular, it is suitable that $R_1$ is a triisopropylsilyloxymethyl group represented by the following formula (3B).

[Chemical formula 10]

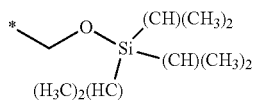

(3B)

(3) Other Decomposable Protecting Groups

Examples of the decomposable protecting group capable of being desorbed from the base to be modified by alkali treatment include an isobutyryl group, a benzoyl group, and an acetoxymethyl group. An example of the decomposable protecting group capable of being desorbed from the base to be modified by acid treatment includes a trityl group. Examples of the decomposable protecting group capable of being desorbed from the base to be modified by oxidation treatment include an allyloxymethyl group, a dimethoxybenzyloxymethyl group, and a trimethoxybenzyloxymethyl group. Examples of the decomposable protecting group capable of being desorbed from the base to be modified by desilylation treatment include a t-butyldimethoxysilyloxymethyl group, and a t-butyldiphenylsilyloxymethyl group. An example of the decomposable protecting group capable of being desorbed from the base to be modified by heat treatment includes an isocyanate group. An example of the decomposable protecting group capable of being desorbed from the base to be modified by esterase treatment includes an acetoxymethyl group. An example of the decomposable protecting group capable of being desorbed from the base to be modified by phosphatase treatment includes a methyl phosphate group.

The primer according to the present invention is particularly a single-stranded DNA or single-stranded RNA to be suitably used for PCR, and is an oligonucleotide or polynucleotide having a structure represented by the above formula (1). The number of base pairs of the primer may be appropriately set depending on, for example, the sequence of a target DNA or the like, and is generally 20 base pairs or less for an oligonucleotide and more than 20 base pairs for a polynucleotide. The upper limit of the number of base pairs of the polynucleotide is not particularly limited, and for example, 40 base pairs or less are preferable as a commonly used primer. Further, the lower limit of the number of base pairs of the oligonucleotide is not particularly limited as long as the oligonucleotide having such a lower limit of the number can be used as a primer, and for example, 5 base pairs or more are preferable as a commonly used primer.

2. Method for Producing Primer

The primer according to the present invention can be produced by synthesizing a modified nucleoside having a structure represented by the following formula (4) (hereinafter, may also be referred to as "nucleoside derivative"), and then ligating an unmodified nucleotide to the modified nucleoside by a solid-phase synthesis method such as a phosphoramidite method:

[Chemical formula 11]

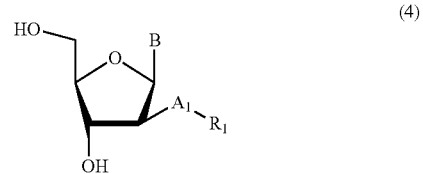

(4)

where, $A_1$ and $R_1$ are as defined in the above formula (1), and B represents a base or a modified base.

As the outline of the method for synthesizing a primer, first, the 3'-hydroxyl group and 5'-hydroxyl group of a nucleoside are protected, the 2'-hydroxyl group is replaced with a linker element $A_1$, a decomposable protecting group $R_1$ is bonded to the linker element $A_1$, and then the 3'-hydroxyl group and 5'-hydroxyl group are deprotected. After that, a phosphoramidite or the like is reacted, and an unmodified nucleotide is ligated by a solid-phase synthesis method to synthesize a primer. Hereinafter, specific methods for producing some primers disclosed in Examples will be described.

(a) Synthesis of nucleoside derivative 1 having photodecomposable protecting group (* compound in which $A_1$ represents —S— group, and $R_1$ represents 2-nitrobenzyloxymethyl group) and of primer

[Chemical formula 12]

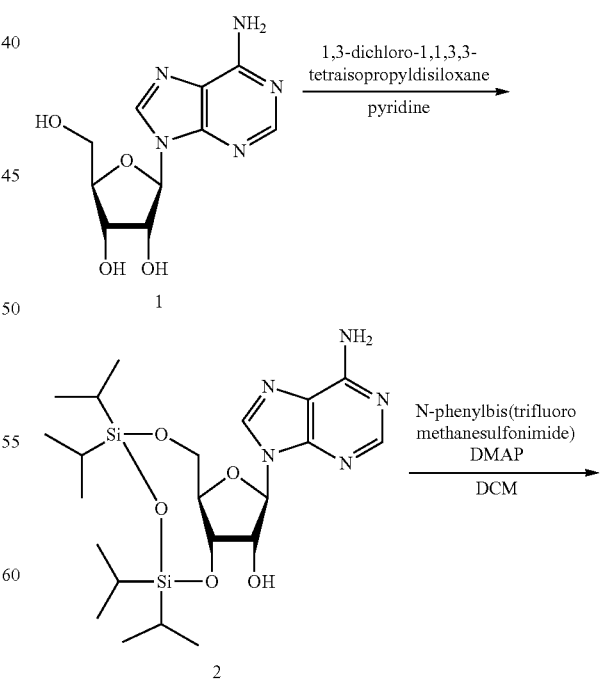

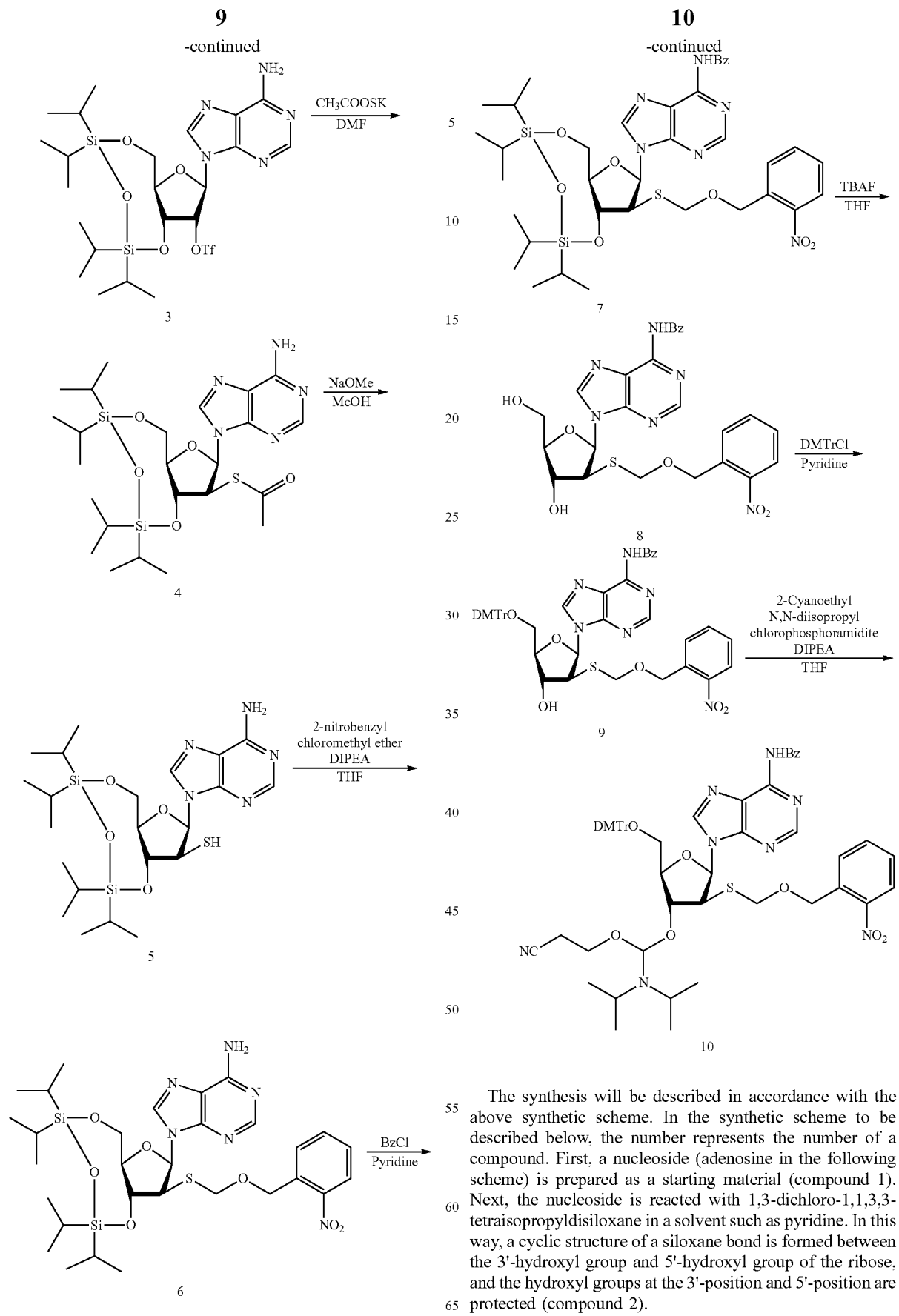

The synthesis will be described in accordance with the above synthetic scheme. In the synthetic scheme to be described below, the number represents the number of a compound. First, a nucleoside (adenosine in the following scheme) is prepared as a starting material (compound 1). Next, the nucleoside is reacted with 1,3-dichloro-1,1,3,3-tetraisopropyldisiloxane in a solvent such as pyridine. In this way, a cyclic structure of a siloxane bond is formed between the 3'-hydroxyl group and 5'-hydroxyl group of the ribose, and the hydroxyl groups at the 3'-position and 5'-position are protected (compound 2).

Next, N-phenyltrifluoromethanesulfonimide is added, a nucleophile such as N,N-dimethyl-4-aminopyridine (DMAP) is reacted in a solvent such as dichloromethane (DCM) to set the 2'-position of the ribose to be a trifluorosulfonic acid group (compound 3). Next, a compound having a thiol group such as potassium thioacetate is reacted in the presence of N,N-dimethylformamide (DMF) or the like to form a thioester at the 2'-position of the ribose (compound 4). Further, the thioester group is converted into a thiol group by performing the reaction in an ammonia/methanol solution (compound 5).

Subsequently, 2-nitrobenzylchloromethyl ester, N,N-diisopropylethylamine (DIPEA), and tetrahydrofuran (THF) are added, and a 2-nitrobenzyloxymethyl group that is a decomposable protecting group is bonded to the thiol (compound 6). Furthermore, benzoyl chloride (BzCl), and pyridine are added, and a benzoyl group is bonded to an amino group of the base (compound 7). In this state, tetra-n-butylammonium fluoride (TBAF), and tetrahydrofuran (THF) are added, and the protecting groups at the 3'- and 5'-positions of the ribose are desorbed to set the positions to be hydroxyl groups (compound 8). In this way, a nucleoside derivative (compound 8) can be synthesized.

Next, in order to produce a primer by ligating another nucleotide to a nucleoside derivative by a phosphoramidite method, a nucleoside derivative is modified. First, 4,4'-dimethoxytrityl chloride (DMTrCl), and pyridine are added to the nucleoside derivative, and a 4,4'-dimethoxytrityl chloride group is bonded to the 5'-hydroxyl group of the ribose (compound 9). Next, 2-cyanoethyl N,N-diisopropylchlorophosphoramidite is added to THF, and DIPEA, and the phosphoramidite is bonded to the 3'-hydroxyl group of the ribose (compound 10). After that, by a routine procedure, the nucleotides are solid-phase synthesized so that a desired sequence is obtained, and thus a primer is synthesized.

(b) Synthesis of nucleoside derivative 3 having fluorine decomposable protecting group (* compound in which $A_1$ represents —S— group, and $R_1$ represents triisopropylsilyloxymethyl group) and of primer

[Chemical formula 13]

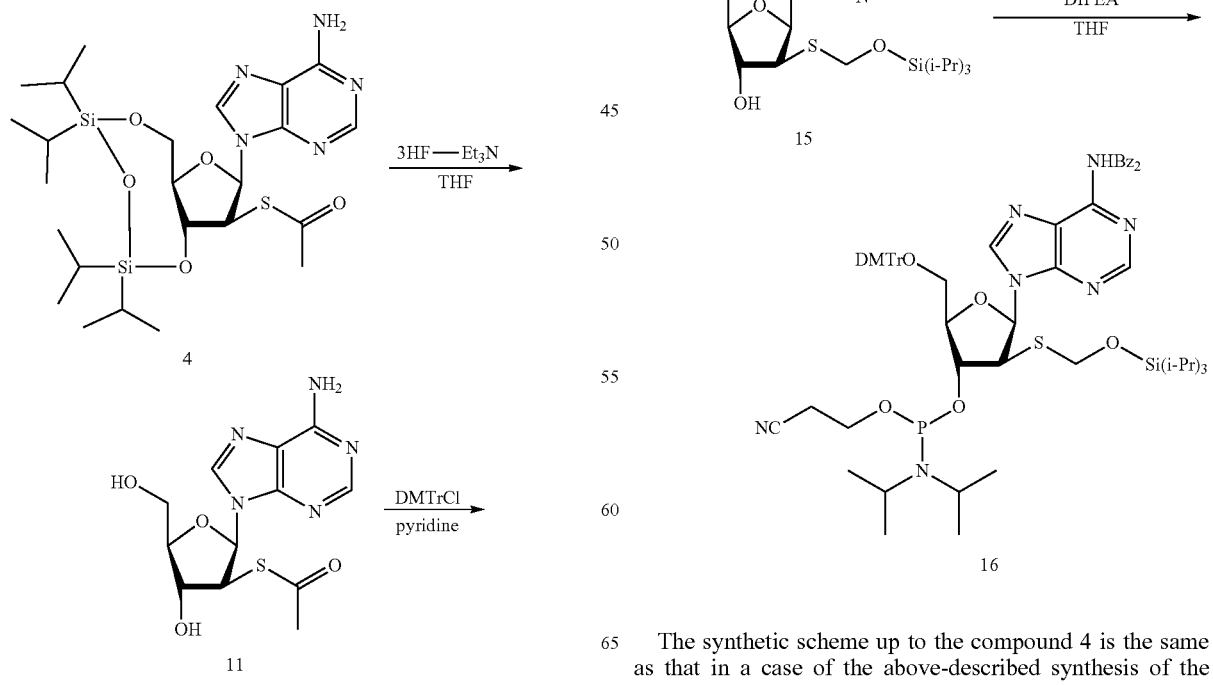

The synthetic scheme up to the compound 4 is the same as that in a case of the above-described synthesis of the nucleoside derivative 1. Next, a fluorine compound such as 3HF-Et$_3$N (the molar ratio of anhydrous hydrogen fluoride (HF) to triethylamine (Et$_3$N) is 3:1), and THF are added, and the protecting groups at the 3'- and 5'-positions of the ribose are desorbed to set the positions to be hydroxyl groups (compound 11). Subsequently, DMTrCl, and pyridine are added, and a 4,4'-dimethoxytrityl chloride group is bonded to the 5'-hydroxyl group of the ribose (compound 12). Next, a silane compound such as chloromethoxy triisopropylsilane (TOMCl) is reacted in the presence of ammonia methanol (NH$_3$-MeOH), DMF, or the like, and a triisopropylsilyloxymethyl group is bonded to the 2'-position of the ribose (compound 13).

Next, in order to produce a primer by ligating another nucleotide to a nucleoside derivative by a phosphoramidite method, a nucleoside derivative is modified. First, chlorotrimethylsilane (TMSCl), BzCl, and pyridine are added, a benzoyl group is bonded to an amino group of the base, and trimethylsilane is bonded to the 3'-hydroxyl group of the ribose (compound 14). Next, HF, and pyridine are reacted, and the 3'-position of the ribose is set to be a hydroxyl group (compound 15). Further, a phosphoramidite is bonded to the 3'-hydroxyl group of the ribose similarly as in a case of the synthesis of the nucleoside derivative 1 (compound 16).

(c) Synthesis of nucleoside derivative 3 having photodecomposable protecting group (* compound in which A$_1$ represents —Se— group, and R$_1$ represents 2-nitrobenzyloxymethyl group) and of primer

[Chemical formula 14]

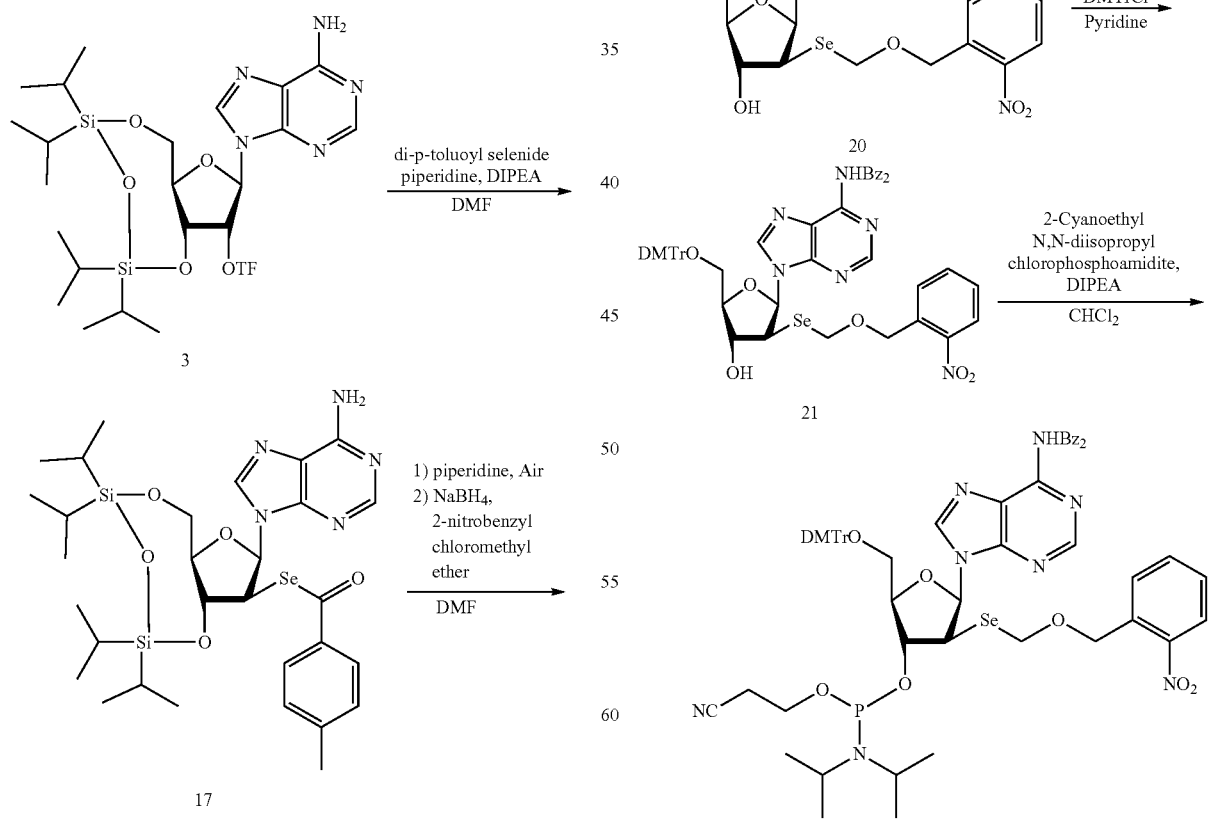

The synthetic scheme up to the compound 3 is the same as that in a case of the above-described synthesis of the nucleoside derivative 1. Next, di-p-toluoyl selenide, piperidine, and DIPEA are reacted in a solvent such as DMF (compound 17). Further, piperidine, air, NaBH4, and 2-nitrobenzylchloromethyl ester are reacted in a solvent such as DMF, and a seleno compound having a photodecomposable protecting group at the 2'-position of the ribose is bonded (compound 18).

After that, the treatment is performed in a similar manner as in the synthetic scheme of a nucleoside derivative 1, and compounds 19 to 20 are synthesized sequentially. Further, another nucleotide is ligated to a nucleoside derivative by a phosphoramidite method, and a primer is produced. In this case, the treatment is also performed in a similar manner as in the synthetic scheme of a nucleoside derivative 1, and compounds 21 and 22 are synthesized sequentially.

3. Method for and Device for Producing Double-Stranded DNA Having Sticky Ends

Next, a method for and a device for producing double-stranded DNA having sticky ends will be described. The device for producing double-stranded DNA according to the present invention is a device for providing sticky ends by using the primer according to the present invention. Further, the method for producing double-stranded DNA according to the present invention is a method for providing sticky ends by using the primer according to the present invention with the use of a template DNA containing a target DNA sequence. Hereinafter, the method and the device will be described with reference to FIG. 1.

First, a primer set for PCR amplification containing a forward primer and a reverse primer as reagents is prepared (preparation step). The forward primer is complementary to a part of a sequence of the antisense strand of the template DNA, and has a structure represented by the formula (1). Further, the reverse primer is complementary to a part of a sequence of the sense strand of the template DNA, and has a structure represented by the formula (1).

As shown in (a) of the diagram, the forward primer and the reverse primer are sequenced so as to sandwich the target DNA sequence to be amplified. Further, the primers are designed so that the position of a nucleotide having a decomposable protecting group of the formula (1) in the primer is a position adjacent to the 5'-end side of the nucleotide on the most 5'-end side on the 5'-recessed side in the sequence of the sticky end to be targeted ((d) in the diagram). That is, the nucleotide on the 3'-end side adjacent to the nucleotide having a structure of the formula (1) is set to be a nucleotide at the 5'-end of the sticky end. Other reagents include polymerase (such as Taq polymerase) used for PCR, a buffer, and a dNTP.

Next, the sequence of a template DNA is amplified by using a PCR device (amplification unit) (amplification step). In the PCR device, multiple cycles of polymerase chain reaction (PCR) are performed by using a template DNA as the template, a forward-side extended chain in which the forward primer is extended, and a reverse-side extended chain in which the reverse primer is extended are formed, the forward-side extended chain and the reverse-side extended chain are annealed, and double-stranded DNA with 3'-recessed ends ((b) in the diagram) is formed.

In the PCR, the sequence of a template DNA is amplified by repeating thermal denaturation, annealing, and extension reaction. Although depending on the PCR conditions, the thermal denaturation is performed at around 95° C. for 1 to 3 minutes, the annealing is performed at a temperature of the primer ±5° C., and the extension reaction is performed for 1 to 10 minutes. The number of PCR cycles is not particularly limited, and in general, around 24 to 40.

As shown in the diagram, double-stranded DNA with 3'-recessed ends is contained in the PCR amplification product. This is because the decomposable protecting group of the formula (1) inhibits the polymerase reaction and terminates the reaction when the complementary strand is synthesized by using a primer as the template.

Next, as shown in (c) of the diagram, the 3'-recessed end is set to be a blunt end by fill-in reaction by Klenow fragment (blunting unit) (blunting step). Examples of the reagent for this reaction include a dNPT, and a buffer, in addition to Klenow fragment (enzyme). The conditions of the fill-in reaction may be appropriately set, and for example, under the conditions of 37° C. for 10 to 30 minutes and then 70° C. for 10 minutes, the enzyme is inactivated.

After that, as shown in (d) of the diagram, $R_1$ is deprotected by a predetermined treatment, the single-stranded DNA is cleaved at a structural part of the formula (1) to form a sticky end with a 3'-protruding end (deprotection cleavage step). The predetermined treatment is a treatment for deprotecting $R_1$, and examples of the treatment include the above-described photoirradiation treatment, and reduction treatment.

Hereinafter, the cleavage mechanism will be described. As shown in the following formula, when a predetermined treatment is applied, the decomposable protecting group $R_1$ of the formula (1) is desorbed, and hydrogen is bonded to the linker $A_1$. The linker $A_1$ forms a heterocycle consisting of a 3-membered ring of the 2'-carbon and the 3'-carbon of the ribose (for example, a thiirane ring in a case where the $A_1$ is sulfur), and consequently, a phosphate bond at the 3'-carbon is cleaved.

[Chemical formula 15]

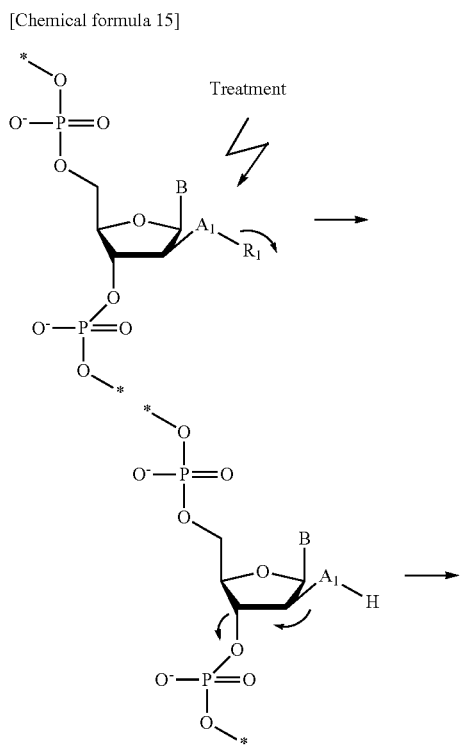

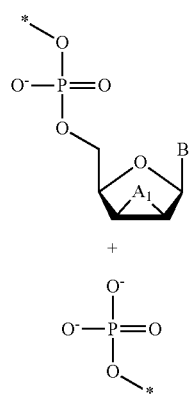

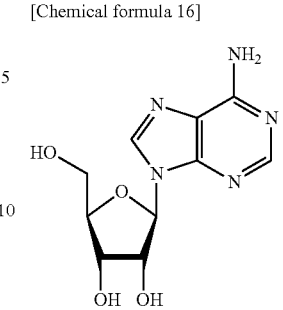

As the photoirradiation treatment, for example, a method of irradiation with light at a wavelength of 300 to 400 nm for 1 to 30 minutes by a light source device (deprotection cleavage unit) can be mentioned. Further, as the reduction treatment, for example, a method of performing the treatment, for example, at 70 to 80° C. for 1 to 30 minutes by using fluoride ions of tetra-n-butylammonium fluoride (TBAF) or the like can be mentioned. In this way, the single-stranded DNA on the 5'-end side containing the nucleoside of the formula (1) of a primer is cleaved, and double-stranded DNA having 3'-protruding ends (5'-recessed ends) can be synthesized. Similarly, also in other treatments, the deprotection and the cleavage of single-stranded DNA are performed by using a device for deprotecting a decomposable protecting group (deprotection cleavage device).

In the present invention, the sticky end can be freely designed without using a restriction enzyme or the like, and thus DNA having a desired sequence can be freely ligated. For example, both of the sequences of a target DNA and a vector are designed, a sticky end common to both of the sequences is formed by deprotection cleavage treatment, the ligation is performed to prepare recombinant DNA, and the prepared recombinant DNA can be used for cloning, library preparation, construction of a mass expression system, or the like. Further, by ligating multiple genome sequences having sticky ends, genome build-up reaction can be performed in vitro. Alternatively, by introducing double-stranded DNA in a blunt-end state into a cell and performing deprotection cleavage treatment in the cell, genome build-up reaction can also be performed in the cell.

EXAMPLES

Hereinafter, the present invention will be specifically described by way of Examples, but these Examples do not limit the object of the present invention. Further, in the following Examples, the expression "%" is on a mass basis (mass percent) unless otherwise particularly specified.

1. Photocleavage Analog (S)

1-1. Synthesis of Photocleavage Analog (A*)

The synthetic scheme of a photocleavage analog is shown below. Hereinafter, the procedure for synthesizing a photocleavage analog will be described in accordance with the synthetic scheme.

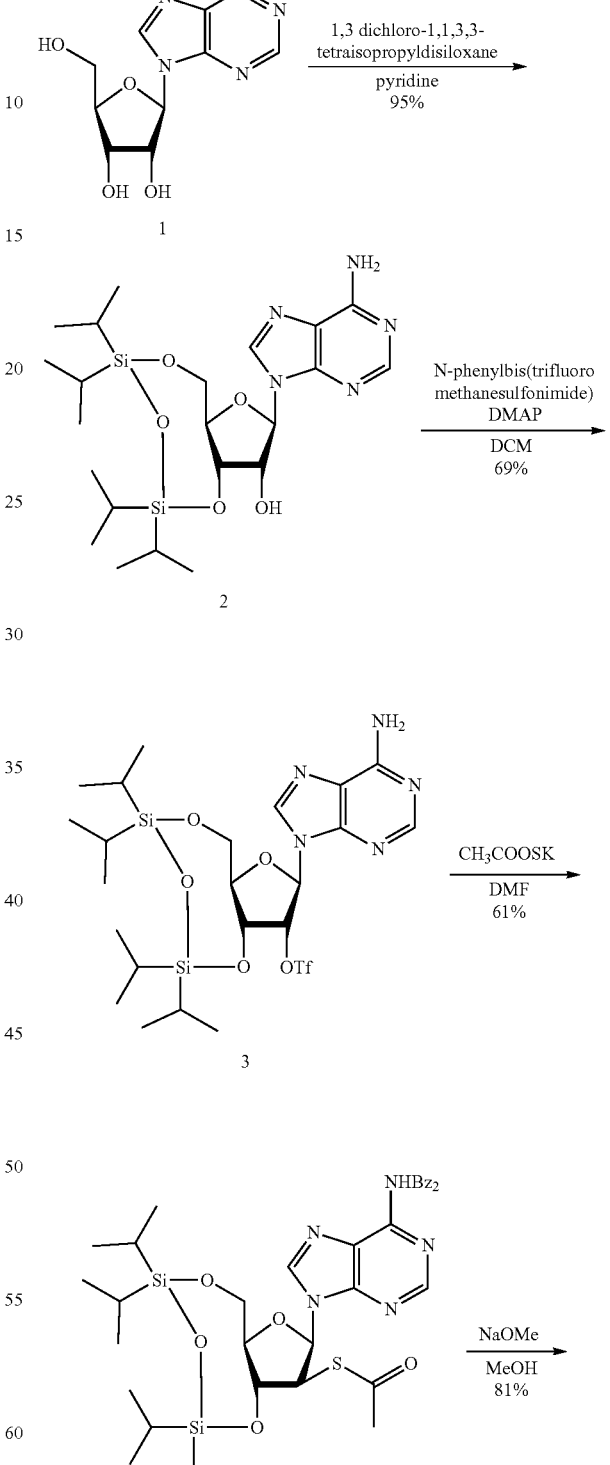

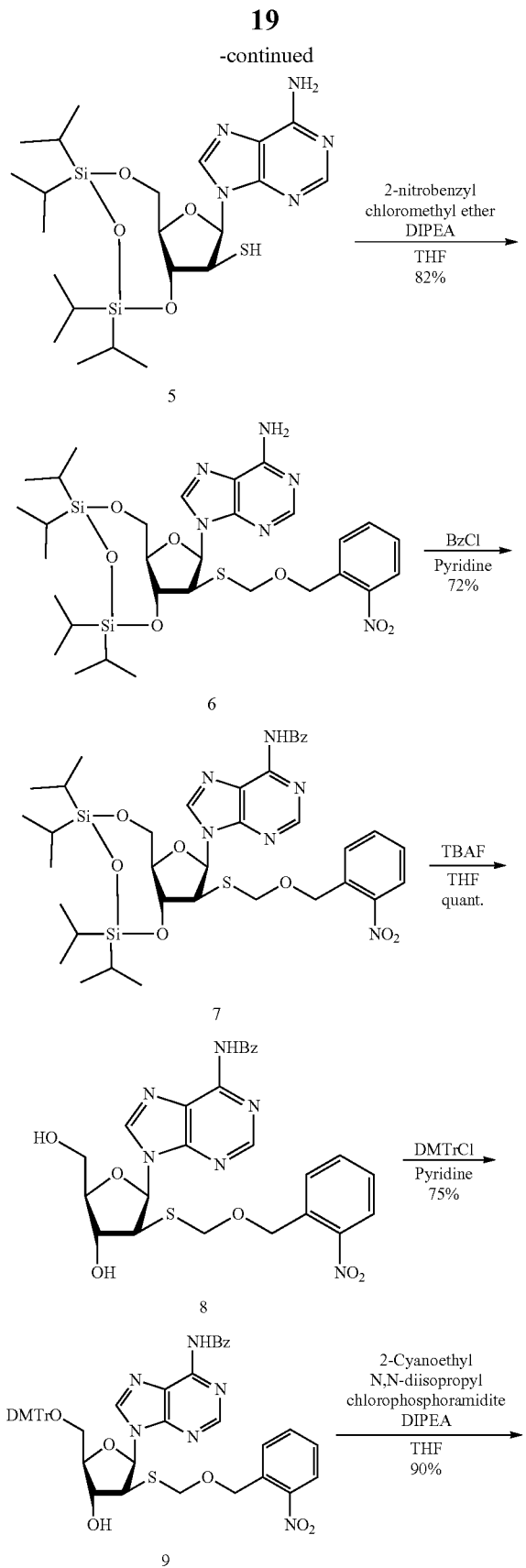

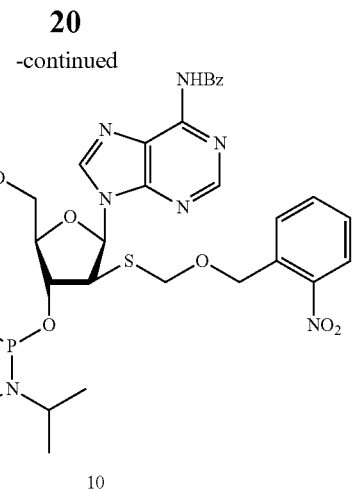

(1) 3',5'-O-(1,1,3,3-Tetraisopropyl-1,3-disiloxanediyl)adenosine (Compound 2)

1,3-Dichloro-1,1,3,3-tetraisopropyldisiloxane (3.9 mL, 12.3 mmol) was added into a solution of adenosine (compound 1, 3.00 g, 11.2 mmol) in pyridine (112 mL), and the reaction mixture was stirred at 0° C. for 1 hour. After that, the reaction mixture was warmed up to room temperature, and was stirred for 5.5 hours. The solvent was evaporated in vacuo, and the residue was extracted with $H_2O$ and $CH_2Cl_2$. The organic phase was washed with a 1M HCl solution, a saturated $NaHCO_3$ solution, and saline, dried ($Na_2SO_4$), and concentrated in vacuo. The obtained residue was purified by silica gel chromatography ($CH_2Cl_2$/MeOH, 100/0 to 95/5 v/v) to obtain a compound 2 (5.43 g, 10.65 mmol, 95%).

$^1$H-NMR (400 MHz, DMSO-$d_6$): δ0.95-1.07 (m, 8H), 3.92 (dd, J=12.8, 2.8 Hz, 1H), 3.97-4.01 (m, 1H), 4.05 (dd, J=12.8, 3.2 Hz, 1H), 4.51 (d, J=5.6 Hz, 1H), 4.79 (dd, J=8.8, 5.2 Hz, 1H), 5.60 (brs, 1H), 5.86 (d, J=1.2 Hz, 1H), 7.30 (brs, 2H), 8.06 (s, 1H), 8.20 (s, 1H); LRMS (ESI$^+$) calc. m/z 510.26 (M+H$^+$), 532.24 (M+Na$^+$), found m/z 510 (M+H$^+$), 532 (M+Na$^+$).

(2) 3',5'-O-(1,1,3,3-Tetraisopropyl-1,3-disiloxanediyl)-2'-O-triflyl-adenosine (Compound 3)

N-Phenyltrifluoromethanesulfonimide (4.57 g, 12.8 mmol) was added at 0° C. into a solution of DMAP (3.90 g, 32.0 mmol) in a solution of a compound 2 (5.43 g, 10.7 mmol) and $CH_2Cl_2$ (106 mL). The reaction mixture was stirred at 0° C. for 1 hour and at room temperature for 2 hours. The mixture was extracted with a cooled 0.1 M AcOH solution and $CH_2Cl_2$. The organic phase was washed with a saturated $NaHCO_3$ solution, and saline, dried ($Na_2SO_4$), and concentrated in vacuo. The obtained residue was purified by silica gel chromatography (hexane/EtOAc, 1/1 v/v) to obtain a compound 3 (4.76 g, 7.42 mmol, 69%).

$^1$H-NMR (400 MHz, DMSO-$d_6$): δ0.98-1.11 (m, 28H), 3.94-4.08 (m, 3H), 5.37 (dd, J=9.6, 5.6 Hz, 1H), 6.08 (d, J=4.8 Hz, 1H), 6.45 (s, 1H), 7.42 (brs, 2H), 8.03 (s, 1H), 8.26 (s, 1H); LRMS (ESI$^+$) calc. m/z 642.21 (M+H$^+$), 664.19 (M+Na$^+$), found m/z 642 (M+H$^+$), 664 (M+Na$^+$).

(3) 9-[3,5-O-(1,1,3,3-Tetraisopropyl-1,3-disiloxanediyl)-2-deoxy-2-acetylthio-β-D-arabinofuranosyl]adenine (Compound 4)

A compound 3 (1.06 g, 1.65 mmol) and $CH_3COOSK$ (302 mg, 2.64 mmol) was dissolved in DMF (4.1 mL), and the obtained mixture was stirred at room temperature for 20 hours. The reaction mixture was extracted with a saturated NaHCO$_3$ solution and hexane/EtOAc (1/3 v/v). The organic phase was washed with saline, dried (Na$_2$SO$_4$), and concentrated in vacuo. The obtained residue was purified by silica gel chromatography (hexane/EtOAc, 2/1 to 1/2 v/v) to obtain a compound 4 (0.57 g, 1.00 mmol, 61%).

$^1$H-NMR (400 MHz, DMSO-d$_6$): δ1.01-1.18 (m, 28H), 2.19 (s, 3H), 3.89-3.98 (m, 2H), 4.17 (dd, J=11.6, 6.4 Hz, 1H), 4.62 (dd, J=10, 8.0 Hz, 1H), 5.26 (t, J=8.0 Hz, 1H), 6.39 (d, J=8.0 Hz, 1H), 7.34 (brs, 2H), 8.02 (s, 1H), 8.10 (s, 1H); HRMS (ESI$^+$) calc. m/z 568.24 (M+H$^+$), 590.23 (M+Na$^+$), found m/z 568.2467 (M+H$^+$), 590.2286 (M+Na$^+$).

(4) 9-[3,5-O-(1,1,3,3-Tetraisopropyl-1,3-disiloxanediyl)-2-deoxy-2-thio-β-D-arabinofuranosyl]adenine (Compound 5)

A 28% MeOH solution of sodium methoxide in a catalyst amount was added into a solution of a compound 4 (2.11 g, 3.72 mmol) in MeOH (25 mL). The obtained mixture was stirred at room temperature for 4 hours, and was extracted with H$_2$O and EtOAc. The organic phase was washed with H$_2$O, and saline, dried (Na$_2$SO$_4$), and concentrated in vacuo to obtain a compound (1.96 g, 3.72 mmol, quant).

$^1$H-NMR (400 MHz, CDCl$_3$): δ1.04-1.14 (m, 21H), 1.18 (s, 7H), 3.81-3.92 (m, 2H), 4.06 (dd, J=13.2, 3.2 Hz, 1H), 4.22 (dd, J=13.2, 3.6 Hz, 1H), 4.60-4.65 (m, 1H), 5.64 (s, 1H), 6.38 (d, J=7.2 Hz, 1H), 8.10 (s, 1H), 8.34 (s, 1H).

(5) 9-[3,5-O-(1,1,3,3-Tetraisopropyl-1,3-disiloxanediyl)-2-deoxy-2-(2-nitrobenzyloxymethyl)thio-β-D-arabinofuranosyl]adenine (Compound 6)

A 1.3 M solution of 2-nitrobenzyloxymethyl chloride (1 mL, 1.30 mmol) was added at 0° C. into a solution of a compound 5 (0.53 g, 1.00 mmol) and DIPEA (524 μL, 1.30 mmol) in CH$_2$Cl$_2$ (4.0 mL), and the obtained mixture was stirred for 1 hour. The mixture was extracted with H$_2$O and CH$_2$Cl$_2$. The organic phase was washed with a saturated NaHCO$_3$ solution, and saline, dried (Na$_2$SO$_4$), and concentrated in vacuo. The obtained residue was purified by silica gel chromatography (CH$_2$Cl$_2$/MeOH, 50/1 to 20/1 v/v) to obtain a compound 6 (0.57 g, 0.82 mmol, 82%).

$^1$H-NMR (400 MHz, CDCl$_3$)): δ1.00-1.11 (m 21H), 1.17 (s, 7H), 3.88-3.98 (m, 2H), 4.04 (dd, J=12.8, 2.8 Hz, 1H), 4.19 (dd, J=13.2, 4.4 Hz, 1H), 4.67-4.84 (m, 5H), 7.44-7.48 (m, 1H), 7.62-7.72 (m, 2H), 7.94 (s, 1H), 8.07 (dd, J=8.0, 1.2 Hz, 1H), 8.23 (s, 1H).

(6) N$^6$-Benzoyl-9-[3,5-O-(1,1,3,3-tetraisopropyl-1,3-disiloxanediyl)-2-deoxy-2-(2-nitrobenzyloxymethyl)thio-β-D-arabinofuranosyl]adenine (Compound 7)

Benzoyl chloride (282 μL, 2.43 mmol) was added into a solution of a compound 6 (0.56 g, 0.81 mmol) in pyridine (5 mL), and the obtained mixture was stirred at room temperature for 3 hours. The mixture was cooled to 0° C., H$_2$O (2 mL) was added into the cooled mixture, and the obtained mixture was stirred for 0.5 hours. Into the resultant mixture, conc. NH$_3$ (aqueous solution) (2 mL) was added, and the mixture was stirred for 0.5 hours. The reaction mixture was extracted with H$_2$O and EtOAc. The organic phase was washed with a saturated NaHCO$_3$ solution, and saline, dried (Na$_2$SO$_4$), and concentrated in vacuo. The obtained residue was purified by silica gel chromatography (hexane/EtOAc, 1/1 v/v) to obtain a compound 7 (0.46 g, 0.58 mmol, 72%).

$^1$H-NMR (400 MHz, CDCl$_3$): δ1.01-1.10 (m, 21H), 1.18 (s, 8H), 3.93-4.09 (m, 2H), 4.21 (dd, J=12.8, 3.6 Hz, 1H), 4.69-4.83 (m, 5H), 7.46-7.56 (m, 3H), 7.60-7.69 (m, 3H), 7.96 (dd, J=8.0, 1.2 Hz, 1H), 8.05-8.11 (m, 2H), 8.73 (s, 1H), 8.79 (dd, J=5.2, 1.6 Hz, 1H).

(7) N$^6$-Benzoyl-9-[2-deoxy-2-(2-nitrobenzyloxymethyl)thio-β-D-arabinofuranosyl]adenine (Compound 8)

TBAF (1 M in THF, 1.2 mL) was added into a solution of a compound 7 (0.47 g, 0.59 mmol) in THF (5 mL), and the obtained mixture was stirred at room temperature for 1.5 hours. The reaction mixture was concentrated in vacuo, and the obtained residue was purified by silica gel chromatography (CH$_2$Cl$_2$/EtOAc, 50/1 to 20/1 v/v) to obtain a compound 8 (0.33 g, 0.59 mmol, quantitative).

$^1$H-NMR (400 MHz, CDCl$_3$): δ3.16 (d, J=5.6 Hz, 1H), 3.64-3.70 (m, 1H), 3.73-3.78 (m, 1H), 3.80-3.84 (m, 1H), 3.97 (dd, J=7.2, 2.8 Hz, 1H), 4.38-4.45 (m, 1H), 4.61-4.84 (m, 4H), 5.12 (t, J=5.6 Hz, 1H), 5.85 (d, J=6.0 Hz, 1H), 6.62 (d, J=7.6 Hz, 1H), 7.53-7.59 (m, 3H), 7.62-7.67 (m, 2H), 7.73-7.77 (m, 1H), 8.02-8.06 (m, 3H), 8.61 (d, J=4.8 Hz, 2H), 11.11 (s, 1H).

(8) N$^6$-Benzoyl-9-[5-O-(4,4'-dimethoxytrityl)-2-deoxy-2-(2-nitrobenzyloxymethyl)thio-β-D-arabinofuranosyl]adenine (Compound 9)

4,4-Dimethoxytrityl chloride (0.24 g, 0.71 mmol) was added into a solution of a compound 8 (0.33 g, 0.59 mmol) in pyridine (4.0 mL). The reaction mixture was stirred at room temperature for 7.5 hours. The mixture was extracted with H$_2$O and EtOAc. The organic phase was washed with a saturated NaHCO$_3$ solution, and saline, dried (Na$_2$SO$_4$), and concentrated in vacuo. The obtained residue was purified by silica gel chromatography (CH$_2$Cl$_2$/MeOH, 60/1 to 20/1 v/v) to obtain a compound 9 (0.38 g, 0.44 mmol, 72%).

$^1$H-NMR (400 MHz, CDCl$_3$): δ1.04 (d, J=6.0 Hz, 5H), 2.17 (s, 1H), 3.18 (d, J=3.2 Hz, 1H), 3.56 (d, J=4.4 Hz, 2H), 3.78 (d, J=1.2 Hz, 6H), 3.85 (dd, J=7.6, 1.6 Hz, 1H), 4.07-4.11 (m, 1H), 4.62-4.71 (m, 3H), 4.84 (d, J=12. Hz, 1H), 4.94 (d, J=14.4 Hz, 1H), 6.65 (d, J=7.6 Hz, 1H), 6.80-6.83 (m, 4H), 7.20-7.33 (m, 4H), 7.42-7.64 (m, 7H), 8.03-8.06 (m, 3H), 8.20 (s, 1H), 8.72 (s, 1H), 9.07 (s, 1H).

(9) N$^6$-Benzoyl-9-{3-O-[2-cyanoethoxy(diisopropylamino)phosphanyl]-5-O-(4,4'-dimethoxytrityl)-2-deoxy-2-(2-nitrobenzyloxymethyl)thio-β-D-arabinofuranosyl}adenine (Compound 10)

2-Cyanoethyl N,N-diisopropylchlorophosphoramidite (241 μL, 1.08 mmol) was added into a solution of a compound 9 (0.42 g, 0.49 mmol) and DIPEA (417 μL, 2.45 mmol) in THF (2.5 mL), the obtained mixture was stirred at room temperature for 1 hour. The reaction mixture was extracted with a saturated NaHCO$_3$ solution and EtAc. The organic phase was washed with saline, dried (Na$_2$SO$_4$), and concentrated in vacuo. The obtained residue was purified by silica gel chromatography (hexane/EtOAc, 1/2 v/v) to obtain a compound 10 (0.46 g, 0.49 mmol, 90%). $^{31}$P-NMR (159 MHz, CDCl$_3$): δ150.4, 150.7.

1-2. Cleavage Reaction of Oligonucleotide Containing Photocleavage Analog (A*)

FIG. 2 is a diagram showing the experiment, which shows that cleavage reaction of an oligonucleotide containing a photocleavage analog depends on photoirradiation and heating. (a) of the diagram shows chemical formulas showing the 20-mer oligonucleotide sequence used, the structure, and the expected reaction mechanism, and (F) represents modification with a fluorescein group. (b) of the diagram shows the analysis results of denaturing polynucleotide gel electrophoresis of cleavage reaction, and (c) shows a graph showing the quantitative results of cleavage reaction products calculated from the results of electrophoresis shown in (b).

An oligonucleotide (5' fluorescein-d (ACGACTCA*CTATAGGGCGAA) (SEQ ID NO: 1), 1 µM) was mixed in a buffer solution containing 10 mM Tris-HCl (pH 8.5), 50 mM $MgCl_2$, and 10 mM dithiothreitol (DTT).

40 µL of this solution was added to wells of a 96-multi-well plate, and irradiated with light at a wavelength of 365 nm at a light intensity of 4 $mW/cm^2$ for 0, 1, 5, or 10 minutes by a MAX-305 light source device (Asahi Spectra Co., Ltd). Subsequently, the same solution was aliquoted into tubes by 10 µL each, and heated at 72° C. for 0, 5, or 10 minutes. After cooling on ice, 10 µL of 2× formamide loading solution (80 (v/v) % formamide, 50 mM EDTA (pH 8.0)) was added, and the mixture was analyzed by 20% denaturing polyacrylamide gel electrophoresis (PAGE) containing 7.5 M urea. The oligonucleotide in the gel was labeled at the 5' end. The detection was performed with the fluorescence of a fluorescein group by using ChemiDoc XRS+Imaging System (Bio-Rad).

1 µM Oligonucleotide, 10 mM Tris-HCl (pH 8.5), 50 mM $MgCl_2$, and 10 mM DTT (40 µL) were irradiated with light at a wavelength of 365 nm at a light intensity of 4 $mW/cm^2$ for 5 minutes, and heated at 72° C. for 5 minutes. One desalted and concentrated by using a pipette tip packed with ZipTip µ-C18 resin was used as a sample, and the MALDI-TOF molecular weight analysis was performed by ultraflex III (Bruker Daltonics). As the matrix, 3-hydroxypicolinic acid was used. Detection results by a MALDI-TOF MS method of the raw material oligonucleotide (i), ones after deprotection (ii, iii) thereof, and cleavage products (iv, v), which are shown in (a) of the diagram, are shown in the following Table.

TABLE 1

| Molecular species | $[MH]^+$ calculation value | $[MH]^+$ measurement value (difference) |
| --- | --- | --- |
| i | 6869.7 | 6874.4 (+4.7) |
| ii | 6734.6 | 6736.5 (+1.9) |
| iii | 6704.6 | 6708.4 (+3.8) |
| iv | 2931.1 | 2933.7 (+2.6) |
| v | 3775.5 | 3777.5 (+2.0) |

As shown in (b) and (c) of the diagram, it can be understood that the percentage of cleavage products increased under the condition of photoirradiation for 5 minutes, and the percentage of cleavage products further increased under the condition of photoirradiation for 10 minutes. In addition, from (b) of the diagram, it can be understood that the band of the raw material becomes thin and the band of the cleavage products becomes thick under the conditions of, in particular, photoirradiation for 10 minutes and heating for 5 minutes or more, and thus this condition is preferable for the cleavage reaction.

1-3. Cloning Reaction Utilizing Sticky End Formation by Photocleavage Reaction

Hereinafter, the cloning and the transformation will be described with reference to FIG. 3. The diagram shows a method for preparing a GFP expression vector using a photocleavage analog. As the outline, first, PCR reaction is performed by using pET21d and pAcGFP1 as the templates, and a vector fragment and an insert fragment are obtained, respectively. Next, sticky fragments are formed by photoirradiation and heating, and then E. coli is transformed by a mixture of both fragments to obtain a ligation product as a plasmid DNA. Hereinafter, the procedure will be described in detail.

The vector-side fragment was prepared as follows. A reaction mixture [0.5 µM primer chain (pET21d_Fw and pET21d_Rev, Table 2), 0.8 ng/µL pET21d (Novagen), 1× PCR Buffer for KOD-Plus-Neo, 1.5 mM $MgSO_4$, 0.2 mM dNTPs, and 0.02 U/µL KOD-Plus-Neo (TOYOBO CO., LTD.)] was prepared by Applied Biosystems 2720 Thermal Cycler (95° C., 30 seconds→50° C., 30 seconds→72° C., 3 minutes)/cycle under the condition of 30 cycles. Into 200 µL of the reaction mixture after PCR reaction, 2 µL of restriction enzyme DpnI (16 U/µL, TOYOBO CO., LTD.) was added, and the obtained mixture was heated at 37° C. for 1 hour. Into the resultant mixture, 200 µL of a mixture of TE saturated phenol (NACALAI TESQUE, INC.) and chloroform in equal amounts was added, the obtained mixture was vigorously mixed, and then was centrifuged (14,000×g, for 3 minutes) to separate the water layer. Similarly, the reaction mixture was extracted with 200 µL of chloroform, and then 20 µL of 3 M NaOAc (pH 5.2) and 220 µL of isopropyl alcohol were added. After cooling at −30° C. for 1 hour, the mixture was centrifuged (20,000×g, for 20 minutes), and DNA was recovered. The target PCR product was purified by 0.8% Agarose S (Wako Pure Chemical Industries, Ltd.) containing agarose gel electrophoresis (GelRed, Wako Pure Chemical Industries, Ltd). DNA was extracted from a cut-out gel piece by using Wizard SV Gel and PCR Clean-Up System (Promega) (yield: 1.27 µg DNA).

The insert-side fragment was prepared as follows. A reaction mixture [0.5 µM primer chain (pAcGFP1_Fw and pAcGFP1_Rev, Table 2), 0.8 ng/µL pAcGFP1 (TAKARA BIO INC.), 1× PCR Buffer for KOD-Plus-Neo, 1.5 mM $MgSO_4$, 0.2 mM dNTPs, 0.02 U/µL KOD-Plus-Neo] was prepared by Applied Biosystems 2720 Thermal Cycler (95° C., 30 seconds→55° C., 30 seconds→72° C., 1 minute)/cycle under the condition of 30 cycles. Into 100 µL of the reaction mixture after PCR reaction, 1 µL of restriction enzyme DpnI (16 U/µL, TOYOBO CO., LTD.) was added, and the obtained mixture was heated at 37° C. for 1 hour. Into the resultant mixture, 100 µL of a mixture of TE saturated phenol (NACALAI TESQUE, INC.) and chloroform in equal amounts was added, the obtained mixture was vigorously mixed, and then was centrifuged (14,000×g, for 3 minutes) to separate the water layer. Similarly, the reaction mixture was extracted with 200 µL of chloroform, and then 10 µL of 3 M NaOAc (pH 5.2) and 110 µL of isopropyl alcohol were added. After cooling at −30° C. for 1 hour, the mixture was centrifuged (20,000×g, for 20 minutes), and DNA was recovered. The target PCR product was purified by 1.5% Agarose S (Wako Pure Chemical Industries, Ltd.) containing agarose gel electrophoresis (GelRed, Wako Pure Chemical Industries, Ltd). DNA was extracted from a cut-out gel piece by using Wizard SV Gel and PCR Clean-Up System (Promega) (yield: 5.33 µg DNA). The post cleavage PCR primer sequences are shown in the following Table. The A* in the sequence represents a photocleavage analog (FIG. 2).

TABLE 2

| PCR Primer Name | DNA sequence |
|---|---|
| pET21d_Fw | 5' TCCGGCTGCTA*ACAAAGCCCGAAAGGAA 3' (SEQ ID NO: 2) |
| pET21d_Rev | 5' TATCTCCTTCTTA*AAGTTAAACAAAATTATTTC 3' (SEQ ID NO: 3) |
| pAcGFP1_Fw | 5' TAAGAAGGAGATA*TACCATGGTGAGCAAGGGCGCC 3' (SEQ ID NO: 4) |
| pAcGFP1_Rev | 5' TAGCAGCCGGA*TCTCACTTGTACAGCTCATCCAT 3' (SEQ ID NO: 5) |

A vector fragment solution (6 ng/μL DNA, 10 mM Tris-HCl (pH 7.5), 5 mM MgCl$_2$, 10 mM DTT) and an insert fragment solution (8.4 ng/μL DNA, 10 mM Tris-HCl (pH 7.5), 5 mM MgCl$_2$, 10 mM DTT) were each added by 50 μL to wells of a 96-multiwell plate, and irradiated with light at a wavelength of 365 nm at around 4 mW/cm$^2$ for 5 minutes by a handy UV lamp (Funakoshi Co., Ltd). Subsequently, the same two solutions were recovered in one 1.5-mL tube, and heated at 72° C. for 10 minutes. 10 μL of 3 M NaOAc (pH 5.2) and 110 μL of isopropyl alcohol were added, the mixture was cooled at −30° C. for 1 hour, then was centrifuged (20,000×g, for 20 minutes), and DNA was recovered. The DNA was dissolved in 5 μL of water, and of which 4.7 μL was added to 50 μL of E. coli competent cell solution (NEB 5-alpha Competent E. coli (High Efficiency), New England Biolabs). This mixture was applied on LB agar medium containing 50 μg/mL ampicillin sodium, and cultured at 37° C. overnight. Nine clones of ligation products were obtained from the sample to which photoirradiation and heating had been performed. In contrast, two clones of ligation products were obtained from the control sample to which photoirradiation and heating had not been performed.

2. Fluorine Cleavage Analog 2-1. Synthesis of Fluorine Cleavage Analog (A**)

The synthetic scheme of a fluorine cleavage analog is shown below. Hereinafter, the procedure for synthesizing a fluorine cleavage analog will be described in accordance with the synthetic scheme.

[Chemical formula 17]

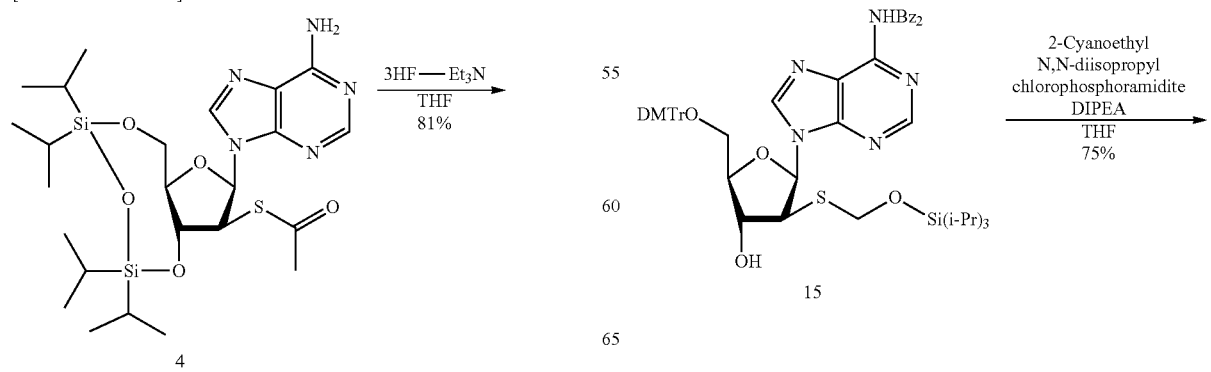

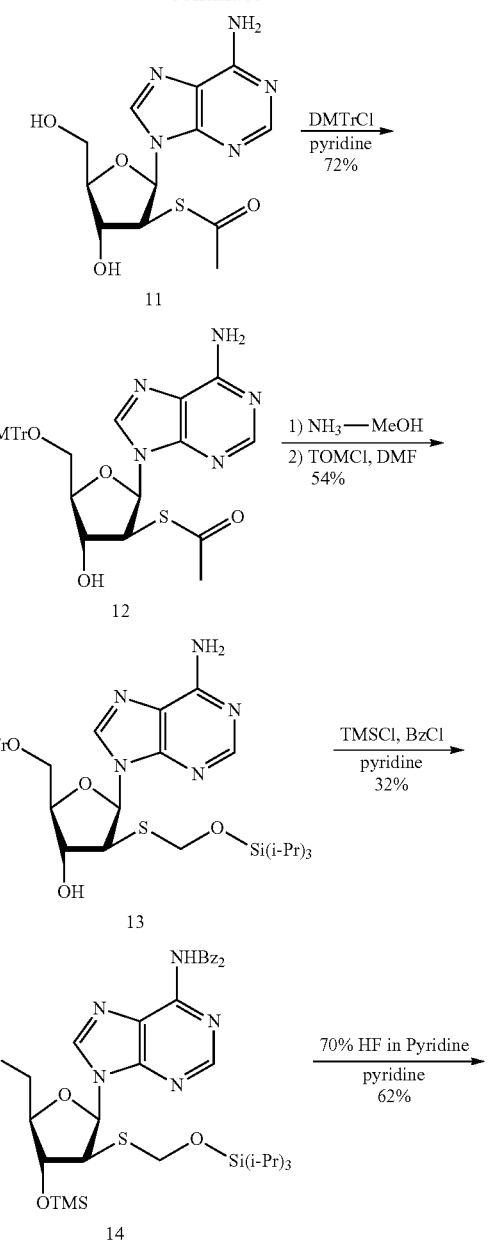

-continued

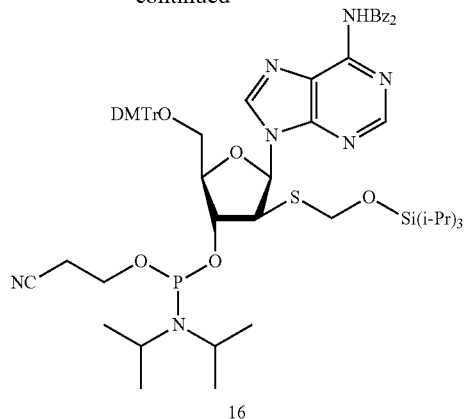

16

(1) 9-[2-Deoxy-2-thio-β-D-arabinofuranosyl]adenine (Compound 11)

3HF-Et₃N (409 μl, 2.51 mmol) was added into a solution of a compound 4 (572 mg, 1.00 mmol) in THF (10 mL), and the reaction mixture was stirred at room temperature for 2 hours. The obtained mixture was concentrated in vacuo. The obtained residue was purified by silica gel chromatography (CHCl₃/MeOH, 92/8 v/v) to obtain a compound 11 (265 mg, 0.81 mmol, 81%).

$^1$H-NMR (400 MHz, DMSO-d₆): δ2.15 (s, 3H), 3.64-3.87 (m, 3H), 4.34 (dd, J=10.0, 7.6 Hz, 1H), 4.50 (dd, J=16.8, 10 Hz, 1H), 5.12 (t, J=5.2 Hz, 1H), 5.80 (d, J=6.4 Hz, 1H), 6.42 (d, J=7.6 Hz, 1H), 7.30 (brs, 2H), 8.10 (s, 1H), 8.22 (s, 1H); HRMS (ESI⁺) calc. m/z 326.09 (M+H⁺), 348.07 (M+Na⁺) found m/z 326.3798 (M+H⁺), 348.0800 (M+Na⁺).

(2) 9-[5-O-(4,4'-Dimethoxytrityl)-2-deoxy-2-thio-β-D-arabinofuranosyl]adenine (Compound 12)

4,4'-Dimethoxytrityl chloride (413 mg, 1.22 mmol) was added into a solution of a compound 11 (265 mg, 0.815 mmol) in pyridine (8.0 mL), and the reaction mixture was stirred at room temperature for 2.5 hours. The reaction mixture was extracted with H₂O and CHCl₃. The organic phase was washed with a saturated NaHCO₃ solution, and saline, dried (Na₂SO₄), and concentrated in vacuo. The obtained residue was purified by silica gel chromatography (CHCl₃/MeOH, 100/0 to 95/5 v/v) to obtain a compound 12 (371 mg, 0.59 mmol, 72%).

$^1$H-NMR (400 MHz, DMSO-d₆): δ2.17 (s, 3H), 3.16 (d, J=8.4 Hz, 1H), 3.45 (dd, J=10.4, 7.6 Hz, 1H), 3.69 (s, 3H), 3.71 (s, 3H), 4.02-4.07 (m, 1H), 4.37 (dd, J=10.0, 8.0 Hz, 1H), 4.67 (dd, J=16.8, 8.4 Hz, 1H), 5.77 (d, J=5.6 Hz, 1H), 6.47 (d, J=8.0 Hz, 1H), 6.72 (d, J=8.8 Hz, 2H), 6.78 (d, J=9.2 Hz, 2H), 7.14-7.21 (m, 7H), 7.29-7.33 (m, 4H), 7.96 (s, 1H), 8.14 (s, 1H); $^{13}$C-NMR (100 MHz, DMSO): δ30.0, 51.2, 54.9, 63.7, 72.2, 82.5, 83.3, 85.4, 112.9, 113.0, 119.1, 126.5, 127.6, 129.6, 129.7, 135.4, 135.5, 140.1, 144.8, 148.7, 152.3, 156.0, 157.9, 158.0, 193.9; HRMS (ESI⁺) calc. m/z 628.22 (M+H⁺), 650.20 (M+Na⁺), found m/z 628.2216 (M+H⁺), 650.2054 (M+Na⁺).

(3) 9-[5-O-(4,4'-Dimethoxytrityl)-2-deoxy-2-triisopropylsilyl oxy methylthio-β-D-arabinofuranosyl]adenine (Compound 13)

28% NaOMe in MeOH (6.0 mL) was added into a solution of a compound 12 (749 mg, 1.19 mmol) in MeOH (6.0 mL). The reaction mixture was stirred at room temperature for 15 minutes, and concentrated in vacuo. The residue was diluted with CH₂Cl₂, and washed with a saturated NaHCO₃ solution and saline. The organic phase was dried (Na₂SO₄), and concentrated in vacuo. The obtained residue was dissolved in THF (12 mL) without further purification. Into the obtained solution, DIPEA (1.4 mL, 8.33 mmol) and (triisopropylsiloxy)methyl chloride (304 μL, 1.31 mmol) were added, and the mixture was stirred at 0° C. for 16.5 hours. The reaction mixture was extracted with H₂O and CH₂Cl₂. The organic phase was washed with a saturated NaHCO₃ solution, and saline, dried (Na₂SO₄), and concentrated in vacuo. The obtained residue was purified by silica gel chromatography (hexane/EtOAc, 1/1 to 1/2 v/v) to obtain a compound 13 (499 mg, 0.65 mmol, 54%).

$^1$H-NMR (400 MHz, DMSO-d₆): δ0.95-1.00 (m, 21H), 3.19 (d, J=8.4 Hz, 1H), 3.45 (dd, J=10.8, 7.6 Hz, 1H), 3.70 (s, 3H), 3.71 (s, 3H), 3.88 (t, J=7.6 Hz, 1H), 3.97-4.01 (m, 1H), 4.49 (dd, J=14.4, 8.8 Hz, 1H), 4.67 (d, J=10.4 Hz, 1H), 4.76 (d, J=10.8 Hz, 1H), 5.75 (d, J=6.0 Hz, 1H), 6.49 (d, J=7.2 Hz, 1H), 6.77 (d, J=8.8 Hz, 2H), 6.81 (d, J=9.2 Hz, 2H), 7.18-7.26 (m, 9H), 7.35-7.36 (m, 2H), 8.02 (s, 1H), 8.11 (s, 1H); $^{13}$C-NMR (100 MHz, DMSO): δ11.2, 17.6, 17.7, 52.5, 54.9, 63.5, 63.8, 74.2, 82.9, 84.0, 85.4, 113.0, 118.7, 126.6, 127.7, 129.6, 135.4, 135.5, 139.4, 144.8, 149.0, 152.3, 155.9, 157.9, 158.0; HRMS (ESI⁺) calc. m/z 794.34 (M+Na⁺), found m/z 794.3113 (M+Na⁺).

(4) N⁶-N⁶-Dibenzoyl-9-[5-O-(4,4'-dimethoxytrityl)-2-deoxy-2-triisopropylsilyl oxy methylthio-3-O-trimethylsilyl-β-D-arabinofuranosyl]adenine (Compound 14)

TMSCl (96 μL, 0.76 mmol) was added at room temperature into a solution of a compound 13 (488 mg, 0.63 mmol) in pyridine (7.0 mL). The obtained mixture was stirred for 1 hour, and then BzCl (218 μL, 1.90 mmol) was added, and the mixture was stirred at room temperature for 2 hours. Into the reaction mixture, H₂O (11 mL) was added, and the obtained mixture was stirred for 10 minutes. Next, a 28% NH₃ aqueous solution (14 mL) was added, and the mixture was stirred for 15 minutes. The reaction mixture was extracted with H₂O and CH₂Cl₂. The organic phase was washed with a saturated NaHCO₃ solution, and saline, dried (Na₂SO₄), and concentrated in vacuo. The obtained residue was purified by silica gel chromatography (hexane/EtOAc, 3/1 to 2/1 v/v) to obtain a compound 14 (211 mg, 0.20 mmol, 32%).

$^1$H-NMR (400 MHz, DMSO-d₆): δ-0.05 (s, 9H), 0.95-1.05 (m, 21H), 3.20 (d, J=8.8 Hz, 1H), 3.39 (dd, J=11.2, 6.8 Hz, 1H), 3.68 (s, 3H), 3.69 (s, 3H), 3.97-4.02 (m, 2H), 4.54-4.63 (m, 3H), 6.68 (d, J=7.6 Hz, 1H), 6.78 (d, J=3.6 Hz, 2H), 6.81 (d, J=3.6 Hz, 2H), 7.15-7.21 (m, 7H), 7.32-7.34 (m, 2H), 7.40 (t, J=8.0 Hz, 4H), 7.55 (t, J=8.0 Hz, 2H), 7.75 (d, J=7.2 Hz, 4H), 8.60 (s, 1H), 8.65 (s, 1H); $^{13}$C-NMR (100 MHz, DMSO-d₆): δ0.3, 11.2, 17.6, 17.7, 52.2, 55.0, 65.8, 69.5, 74.3, 82.7, 84.7, 85.6, 113.1, 126.6, 127.1, 127.7, 128.9, 129.6, 129.7, 133.3, 133.4, 135.2, 135.5, 144.4, 146.1, 150.8, 151.6, 152.4, 158.0, 178.9; HRMS (ESI⁺) calc. m/z 1052.45 (M+H⁺), found m/z 1052.4480 (M+H⁺).

(5) N⁶-N⁶-Dibenzoyl-9-[5-O-(4,4'-dimethoxytrityl)-2-deoxy-2-triisopropylsilyl oxy methylthio-β-D-arabinofuranosyl]adenine (Compound 15)

70% HF in pyridine (11 μL, 0.42 mmol) was added into a solution of a compound 14 (160 mg, 0.15 mmol) in pyridine (1.5 mL), and the reaction mixture was stirred at room temperature for 2 hours. The reaction mixture was extracted with H₂O and CH₂Cl₂. The organic phase was washed with a saturated NaHCO₃ solution, and saline, dried (Na₂SO₄), and concentrated in vacuo. The obtained residue was purified by silica gel chromatography (hexane/EtOAc, 2/1 v/v) to obtain a compound 15 (93 mg, 0.09 mmol, 62%).

$^1$H-NMR (400 MHz, DMSO-d$_6$): δ0.94-1.05 (m, 21H), 3.20 (d, J=8.0 Hz, 1H), 3.46 (dd, J=10.8, 7.6 Hz, 1H), 3.68 (s, 3H), 3.69 (s, 3H), 3.92-4.05 (m, 2H), 4.41 (dd, J=15.2, 8.8 Hz, 1H), 4.65 (d, J=10.4 Hz, 1H), 4.76 (d, J=10.8 Hz, 1H), 6.64 (d, J=7.6 Hz, 1H), 6.78 (d, J=8.0 Hz, 2H), 6.80 (d, J=8.4 Hz, 2H), 7.13-7.21 (m, 7H), 7.31-7.33 (m, 2H), 7.42 (t, J=7.6 Hz, 4H), 7.57 (t, J=7.6 Hz, 2H), 7.75 (d, J=7.6 Hz, 4H), 8.54 (s, 1H), 8.58 (s, 1H); $^{13}$C-NMR (100 MHz, DMSO-d$_6$): δ11.2, 17.6, 17.7, 52.5, 54.9, 63.6, 66.0, 74.1, 83.0, 84.8, 85.4, 113.0, 126.6, 127.1, 127.7, 128.9, 129.5, 129.8, 133.3, 133.5, 135.2, 135.8, 144.6, 146.0, 150.8, 151.6, 152.4, 152.9, 158.0, 171.9; HRMS (ESI$^+$) calc. m/z 980.41 (M+H$^+$), found m/z 980.4331 (M+H$^+$).

(6) N$^6$-N$^6$-Dibenzoyl-9-{3-O-[2-cyanoethoxy(diisopropylamino)phosphanyl]-5-O-(4,4'-dimethoxytrityl)-2-deoxy-2-triisopropylsilyl oxy methylthio-β-D-arabinofuranosyl}adenine (Compound 16)

2-Cyanoethyl N,N-diisopropylchlorophosphoramidite (42 μL, 0.19 mmol) and DIPEA (80 μL, 0.47 mmol) were added into a solution of a compound 15 (93 mg, 0.01 mmol) in THF (950 μL), and the mixture was stirred at room temperature for 1 hour. The reaction mixture was extracted with H₂O and EtOAc. The organic phase was washed with a saturated NaHCO₃ solution, and saline, dried (Na₂SO₄), and concentrated in vacuo. The obtained residue was purified by silica gel chromatography (hexane/EtOAc, 2/1 v/v) to obtain a compound 16 (83 mg, 0.07 mmol, 70%).

$^{31}$P-NMR (159 MHz, DMSO-d$_6$): δ149.1, 149.9, HRMS (ESI$^+$) calc. m/z 1180.52 (M+H$^+$), found m/z 1180.5363 (M+H$^+$).

2-2. Synthesis of Oligonucleotide

An oligonucleotide was synthesized by using a DNA synthesizer on the basis of a phosphoramidite method. 6-FAM amidite (ChemGenes Corporation) was used for the fluorescent labeling at the 5' end. The amidite of each synthesized cleavage analog was set to an acetonitrile solution at a final concentration of 50 mM, and was introduced into a DNA primer by using a DNA synthesizer. The deprotection was performed in accordance with a conventional method, each DNA was purified by 20% PAGE, and the structure was confirmed by using MALDI-TOF/MS (Bruker). The sequences of the synthesized DNAs are shown in the following Table.

TABLE 3

| Sequence | calcd. MS | Observed MS ([M + H]$^+$) |
|---|---|---|
| 5'-FAM-ACGACTCA*CTATAGGGCGAA-3' (SEQ ID NO: 6) | 6672.5 | 6676.2 |
| 5'-FAM-ACGACTCA**CTATAGGGCGAA-3' (SEQ ID NO: 7) | 68923.1 | 6892.6 |
| 5'-TCGGTGCTA*ACAAAGCCCGAAAGGAA-3' (SEQ ID NO: 8) | 8797.8 | 8797.0 |

TABLE 3-continued

| Sequence | calcd. MS | Observed MS ([M + H]$^+$) |
|---|---|---|
| 5'-TATCTCCTTCTTA*AAGTTAAACAAAA TTATTTC-3' (SEQ ID NO: 9) | 10216.7 | 10216.2 |
| 5'-TAAGAAGGAGATA*TACCATGGTGAGC AAGGGCGCC-3' (SEQ ID NO: 10) | 11100.3 | 11100.2 |
| 5'-TAGCAGCCCGGA*TCTCACTTGTACAG CTCATCCAT-3' (SEQ ID NO: 11) | 10046.6 | 10047.3 |

3-3. Cleavage Reaction of Oligonucleotide Containing Fluorine Cleavage Analog (A**)

An oligonucleotide (5' fluorescein-d (ACGACTCA**CTATAGGGCGAA) (SEQ ID NO: 12), 1 μM) was mixed in a buffer solution containing 10 mM Tris-HCl (pH 8.5), 50 mM MgCl₂, and 10 mM dithiothreitol (DTT), and then into the mixture, the same amount of a solution of 1 M TBAF in THF was added, and the obtained mixture was heated at 72° C. for 10 minutes. After cooling on ice, the solvent was removed from the mixture by a centrifugal evaporator, and the residue was dissolved again in 10 μL of 2×formamide loading solution (80 (v/v) % formamide, 50 mM EDTA (pH 8.0)). The obtained sample was analyzed by 20% denaturing polyacrylamide gel electrophoresis (PAGE) containing 7.5 M urea. The oligonucleotide in the gel was labeled at the 5' end. The detection was performed with the fluorescence of a fluorescein group by using ChemiDoc XRS+Imaging System (Bio-Rad). FIG. 4 shows a photograph of electrophoresis gel. As shown in the diagram, it can be understood that the oligonucleotide was cleaved by cleavage reaction.

3. Photocleavage Analog (Se)

3-1. Synthesis of Photocleavage Se Analog (ASe)

The synthetic scheme of a photocleavage analog Se is shown below. Hereinafter, the procedure for synthesizing a photocleavage analog will be described in accordance with the synthetic scheme.

[Chemical formula 18]

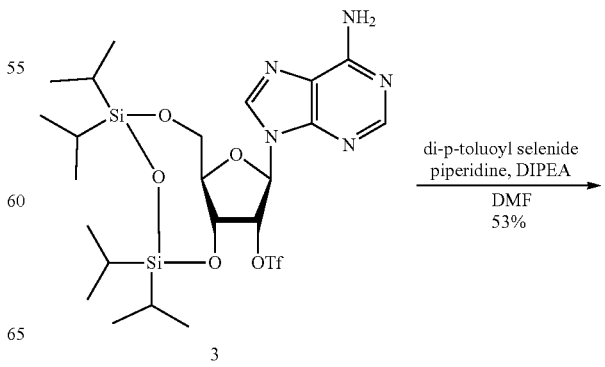

di-p-toluoyl selenide piperidine, DIPEA
DMF
53%

3

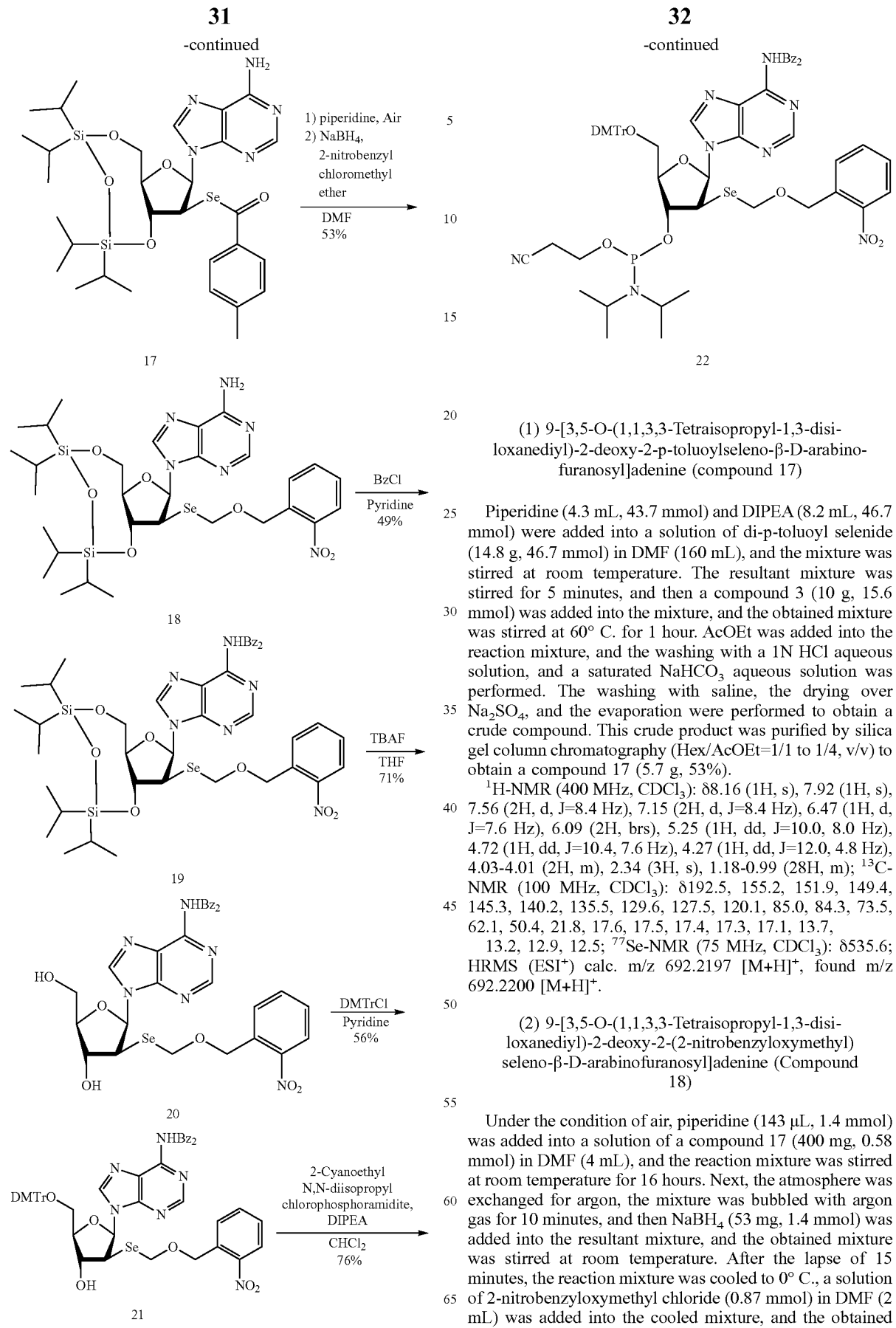

(1) 9-[3,5-O-(1,1,3,3-Tetraisopropyl-1,3-disiloxanediyl)-2-deoxy-2-p-toluoylseleno-β-D-arabinofuranosyl]adenine (compound 17)

Piperidine (4.3 mL, 43.7 mmol) and DIPEA (8.2 mL, 46.7 mmol) were added into a solution of di-p-toluoyl selenide (14.8 g, 46.7 mmol) in DMF (160 mL), and the mixture was stirred at room temperature. The resultant mixture was stirred for 5 minutes, and then a compound 3 (10 g, 15.6 mmol) was added into the mixture, and the obtained mixture was stirred at 60° C. for 1 hour. AcOEt was added into the reaction mixture, and the washing with a 1N HCl aqueous solution, and a saturated NaHCO$_3$ aqueous solution was performed. The washing with saline, the drying over Na$_2$SO$_4$, and the evaporation were performed to obtain a crude compound. This crude product was purified by silica gel column chromatography (Hex/AcOEt=1/1 to 1/4, v/v) to obtain a compound 17 (5.7 g, 53%).

$^1$H-NMR (400 MHz, CDCl$_3$): δ8.16 (1H, s), 7.92 (1H, s), 7.56 (2H, d, J=8.4 Hz), 7.15 (2H, d, J=8.4 Hz), 6.47 (1H, d, J=7.6 Hz), 6.09 (2H, brs), 5.25 (1H, dd, J=10.0, 8.0 Hz), 4.72 (1H, dd, J=10.4, 7.6 Hz), 4.27 (1H, dd, J=12.0, 4.8 Hz), 4.03-4.01 (2H, m), 2.34 (3H, s), 1.18-0.99 (28H, m); $^{13}$C-NMR (100 MHz, CDCl$_3$): δ192.5, 155.2, 151.9, 149.4, 145.3, 140.2, 135.5, 129.6, 127.5, 120.1, 85.0, 84.3, 73.5, 62.1, 50.4, 21.8, 17.6, 17.5, 17.4, 17.3, 17.1, 13.7, 13.2, 12.9, 12.5; $^{77}$Se-NMR (75 MHz, CDCl$_3$): δ535.6; HRMS (ESI$^+$) calc. m/z 692.2197 [M+H]$^+$, found m/z 692.2200 [M+H]$^+$.

(2) 9-[3,5-O-(1,1,3,3-Tetraisopropyl-1,3-disiloxanediyl)-2-deoxy-2-(2-nitrobenzyloxymethyl)seleno-β-D-arabinofuranosyl]adenine (Compound 18)

Under the condition of air, piperidine (143 μL, 1.4 mmol) was added into a solution of a compound 17 (400 mg, 0.58 mmol) in DMF (4 mL), and the reaction mixture was stirred at room temperature for 16 hours. Next, the atmosphere was exchanged for argon, the mixture was bubbled with argon gas for 10 minutes, and then NaBH$_4$ (53 mg, 1.4 mmol) was added into the resultant mixture, and the obtained mixture was stirred at room temperature. After the lapse of 15 minutes, the reaction mixture was cooled to 0° C., a solution of 2-nitrobenzyloxymethyl chloride (0.87 mmol) in DMF (2 mL) was added into the cooled mixture, and the obtained mixture was stirred at 0° C. for 1 hour. The reaction was quenched with the addition of $H_2O$, the mixture was extracted with AcOEt, and the washing with saline, the drying over $Na_2SO_4$, and the evaporation were performed. The crude product was purified by silica gel column chromatography ($CHCl_3$/MeOH=25/1, v/v) to obtain a compound 18 (226 mg, 53%).

$^1$H-NMR (400 MHz, $CDCl_3$): δ8.14 (1H, s), 8.01-7.86 (2H, m), 7.68-7.32 (3H, m), 6.37 (1H, d, J=7.6 Hz), 6.15 (2H, brs), 5.02 (1H, s, diastereotopic), 4.97 (1H, s, diastereotopic), 4.86 (1H, dd, J=10.0, 8.0 Hz), 4.77 (1H, s, diastereotopic), 4.75 (1H, s, diastereotopic), 4.13 (1H, dd, J=12.8, 4.4 Hz), 4.01-3.94 (2H, m), 3.84-3.82 (1H, m), 1.11-0.95 (28H, m); $^{13}$C-NMR (100 MHz, $CDCl_3$): 155.8, 152.8, 149.6, 147.4, 139.2, 133.7, 133.5, 129.1, 128.4, 124.8, 119.6, 84.8, 84.1, 74.9, 69.5, 67.9, 61.6, 48.7, 17.6, 17.5, 17.4, 17.2, 17.1, 17.0, 13.7, 13.1, 13.0, 12.6; $^{77}$Se-NMR (75 MHz, $CDCl_3$): δ231.7; HRMS ($ESI^+$) calc. m/z 739.2204 $[M+H]^+$, found m/z 739.2208 $[M+H]^+$.

(3) $N^6$-$N^6$-Dibenzoyl-9-[3,5-O-(1,1,3,3-tetraisopropyl-1,3-disiloxanediyl)-2-deoxy-2-(2-nitrobenzyloxymethyl)seleno-β-D-arabinofuranosyl]adenine (Compound 19)

Benzoyl chloride (125 μL, 1.08 mmol) was added into a solution of a compound 18 (200 mg, 0.27 mmol) in pyridine (3 mL), and the obtained mixture was stirred at room temperature for 4 hours. AcOEt was added into the reaction mixture, and the washing with $H_2O$ and saline, the drying over $Na_2SO_4$, and the evaporation were performed. The crude product was purified by silica gel column chromatography (hexane/AcOEt=2/1 to 1/2, v/v) to obtain a compound 19 (126 mg, 49%).

$^1$H-NMR (400 MHz, $CDCl_3$): δ8.54 (1H, s), 8.13 (1H, s), 8.04-7.28 (14H, m), 6.47 (1H, d, J=7.6 Hz), 5.05-4.79 (5H, m), 4.19-3.85 (4H, m), 1.13-0.95 (28H, m); $^{13}$C-NMR (100 MHz, $CDCl_3$): δ172.3, 152.9, 152.0, 151.9, 147.6, 143.8, 134.2, 133.7, 133.2, 133.0, 129.6, 129.3, 128.7, 128.6, 128.0, 124.9, 85.4, 84.3, 75.2, 69.7, 68.2, 61.7, 49.1, 17.6, 17.5, 17.4, 17.2, 17.1, 14.2, 13.7, 13.1, 13.0, 12.6; $^{77}$Se-NMR (75 MHz, $CDCl_3$): δ234.4; HRMS ($ESI^+$) calc. m/z 947.2729 $[M+H]^+$, found m/z 947.2727 $[M+H]^+$.

(4) $N^6$-$N^6$-dibenzoyl-9-[2-deoxy-2-(2-nitrobenzyloxymethyl)seleno-β-D-arabinofuranosyl]adenine (Compound 20)

TBAF (1 M in THF, 290 μL) was added into a solution of a compound 19 (125 mg, 0.13 mmol) in THF (1 mL), and the obtained mixture was stirred at room temperature for 1 hour. The reaction mixture was concentrated in vacuo, and the obtained residue was purified by silica gel column chromatography ($CHCl_3$/MeOH=25/1, v/v) to obtain a compound (65 mg, 71%).

$^1$H-NMR (400 MHz, $CDCl_3$): δ8.56 (1H, s), 8.51 (1H, s), 8.02 (1H, d, J=8.0 Hz), 7.81 (4H, d, J=7.2 Hz), 7.60-7.30 (9H, m), 6.55 (1H, d, J=7.6 Hz), 5.02 (2H, s), 4.83-4.69 (3H, m), 3.98-3.75 (4H, m); $^{13}$C-NMR (100 MHz, $CDCl_3$): δ172.4, 152.6, 152.1, 151.9, 147.7, 144.6, 133.9, 133.8, 133.2, 132.7, 130.1, 129.5, 128.9, 128.4, 127.5, 125.0, 86.2, 85.1, 73.5, 69.5, 68.5, 59.9, 49.7; $^{77}$Se-NMR (75 MHz, $CDCl_3$): δ250.1.

(5) $N^6$-$N^6$-Dibenzoyl-9-[5-O-(4,4'-dimethoxytrityl)-2-deoxy-2-(2-nitrobenzyloxymethyl)seleno-β-D-arabinofuranosyl]adenine (Compound 21)

4,4'-Dimethoxytrityl chloride (35 mg, 0.102 mmol) was added into a solution of a compound 20 (60 mg, 0.085 mmol) in pyridine (0.8 mL). The reaction mixture was stirred at room temperature for 2 hours. The reaction mixture was diluted with AcOEt, and washed with saturated $H_2O$. A $NaHCO_3$ aqueous solution. The washing with saline, the drying over $Na_2SO_4$, and the evaporation were performed. The crude product was purified by silica gel column chromatography (hexane/AcOEt=1/1, v/v) to obtain a compound 21 (48 mg, 56%).

$^1$H-NMR (400 MHz, $CDCl_3$): δ8.52 (1H, s), 8.21 (1H, s), 8.03 (1H, d, J=8.0 Hz), 7.83-7.81 (4H, m), 7.57-7.15 (18H, m), 6.79-6.77 (4H, m), 6.60 (1H, d, J=7.2 Hz), 5.04-4.72 (4H, m), 4.66 (1H, dd, J=8.8 Hz), 4.05-4.03 (1H, m), 3.93 (1H, dd, J=8.8, 7.2 Hz), 3.72 (6H, s), 3.52-3.50 (2H, m); $^{13}$C-NMR (100 MHz, $CDCl_3$): δ172.3, 158.7, 152.7, 152.2, 151.9, 147.8, 144.4, 143.8, 135.7, 135.6, 134.2, 133.8, 133.0, 132.5, 130.1, 129.5, 129.0, 128.7, 128.3, 128.0, 127.0, 125.1, 113.3, 86.9, 85.4, 83.3, 76.5, 69.5, 68.6, 62.9, 55.3, 49.6; $^{77}$Se-NMR (75 MHz, $CDCl_3$): δ252.0; HRMS ($ESI^+$) calc. m/z 1007.2513 $[M+H]+$, found m/z 1007.2536 $[M+H]^+$.

(6) $N^6$-$N^6$-Dibenzoyl-9-{3-O-[2-cyanoethoxy(diisopropylamino)phosphanyl]-5-O-(4,4'-dimethoxytrityl)-2-deoxy-2-(2-nitrobenzyloxymethyl)seleno-β-D-arabinofuranosyl}adenine (Compound 22)

2-Cyanoethyl N,N-diisopropylchlorophosphoramidite (25 μL, 0.11 mmol) was added into a solution of a compound DIPEA (47 μL, 0.27 mmol) in 21 (45 mg, 0.045 mmol) and $CH_2Cl_2$ (0.5 mL), the obtained mixture was stirred at 0° C. for 1 hour. The reaction mixture was diluted with AcOEt, and the washing with a saturated $NaHCO_3$ aqueous solution and saline, the drying over $Na_2SO_4$, and the evaporation were performed. The crude product was purified by silica gel column chromatography (hexane/AcOEt=1/1, v/v) to obtain a compound 21 (41 mg, 76%).

$^{31}$P-NMR (159 MHz, $CDCl_3$): δ150.6, 150.3; HRMS ($ESI^+$) calc. m/z 1207.3592 $[M+H]+$, found m/z 12707.3624 $[M+H]+$.

3-2. Synthesis of Oligonucleotide

The amidite of the synthesized cleavage analog $A_{Se}$ was set to an acetonitrile solution at a final concentration of 50 mM, and a DNA oligomer was synthesized by using a DNA synthesizer on the basis of a phosphoramidite method. The deprotection was performed in accordance with a conventional method, the DNA oligomer was purified by reversed-phase HPLC [LaChrom Elite manufactured by Hitachi High-Tech Science Corporation, column: Hydrosphere C18 (250×10 mm) manufactured by YMC CO., LTD.], and the structure was confirmed by using MALDI-TOF/MS (Bruker). The sequences of the synthesized DNAs are shown in the following Table.

TABLE 4

| Sequence |
|---|
| 5'-ACGACTCA$_{Se}$CTATAGGGCGAATTCGAGCTCGGT-3' (SEQ ID NO: 13) |

3-3. Cleavage Reaction of Oligonucleotide Containing Photocleavage Analog ($A_{Se}$)

An oligonucleotide (3 μM) was mixed in a buffer solution containing 10 mM Tris-HCl (pH 8.5), 5 mM $MgCl_2$, and 10 mM dithiothreitol (DTT), and then the mixture was irradiated with light at a wavelength of 365 nm at around 4 mW/cm$^2$ for 10 minutes by a photoirradiation device MAX-305 (Asahi Spectra Co., Ltd.). The obtained sample was diluted twice with a formamide loading solution (80 (v/v) % formamide, 50 mM EDTA (pH 8.0)), and then the diluted sample solution was analyzed by 15% denaturing polyacrylamide gel electrophoresis (PAGE) containing 7.5 M urea. The oligonucleotide in the gel was stained with SYBR Green II Nucleic Acid Gel Stain, and the detection was performed by using ChemiDoc XRS+Imaging System (Bio-Rad). The results are shown in FIG. 5. From these results, a cleavage product was observed by the photoirradiation for 10 minutes under room temperature in the buffer solution.

The invention claimed is:

1. A primer for amplifying a nucleic acid, having a structure represented by the following formula (1):

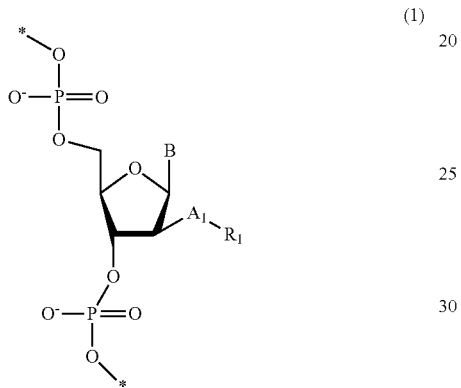

where $A_1$ represents —S—, —S—S—, or —Se—, B represents a base, a symbol * represents a bond to a sugar of an adjacent nucleotide, and $R_1$ is represented by:

a photodecomposable protecting group represented by the following formula (2A):

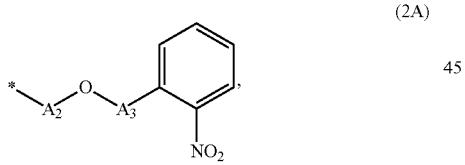

wherein $A_2$ represents an alkylene group having 1 to 3 carbon atoms, $A_3$ represents an alkylene group having 1 to 3 carbon atoms, and a symbol * represents a bond to $A_1$; or a fluoride decomposable protecting group represented by the following formula (2B):

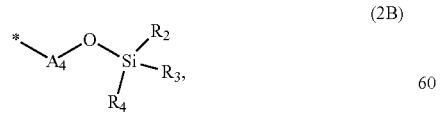

where $A_4$ represents an alkylene group having 1 to 3 carbon atoms, $R_2$ to $R_4$ each represent a straight or branched alkyl group having 1 to 4 carbon atoms, the $R_2$ to $R_4$ may be the same as or different from each other, and a symbol * represents a bond to $A_1$.

2. The primer according to claim 1, wherein the $R_1$ is a 2-nitrobenzyloxymethyl group represented by the following formula (3A):

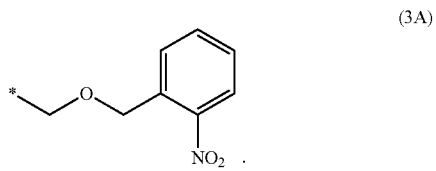 [SMILES: *COCc1ccccc1[N+](=O)[O-]]

3. The primer according to claim 1, wherein the $R_1$ is a triisopropylsilyloxymethyl group represented by the following formula (3B):

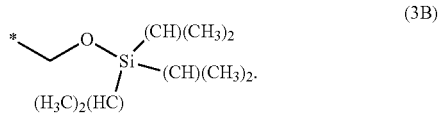

4. A device for producing double-stranded DNA having sticky ends by using a primer for amplifying a nucleic acid, the device comprising:

a forward primer being complementary to a part of a sequence of an antisense strand of a template DNA to be used as a template and having a structure represented by the following formula (1):

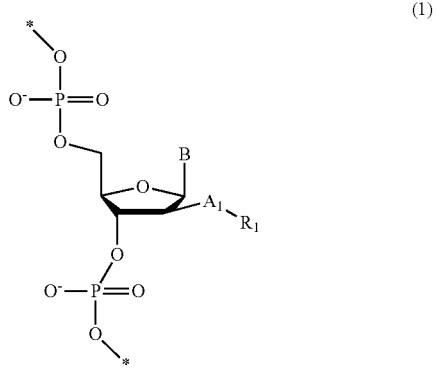

where $A_1$ represents —S—, —S—S—, or —Se—, B represents a base, $R_1$ represents a decomposable protecting group, and a symbol * represents a bond to a sugar of an adjacent nucleotide;

a reverse primer being complementary to a part of a sequence of a sense strand of the template DNA and having the structure represented by formula (1);

an amplification unit for performing a plurality of cycles of polymerase chain reaction (PCR) by using the template DNA as a template to form a forward-side extended chain being the forward primer extended and a reverse-side extended chain being the reverse primer extended, and for annealing the forward-side extended chain and the reverse-side extended chain to form double-stranded DNA with 3'-recessed ends;

a blunting unit for making the 3' ends of the double-stranded DNA blunt by Klenow fragment; and a deprotection cleavage unit for deprotecting the $R_1$, and cleaving DNA at the bond at the 3'-carbon of formula (1) to form a sticky end with a 3'-protruding end.

5. A method for producing double-stranded DNA having sticky ends by using a primer for amplifying a nucleic acid, the method comprising:

a preparation step of preparing a forward primer being complementary to a part of a sequence of an antisense strand of a template DNA to be used as a template and having a structure represented by the following formula (1):

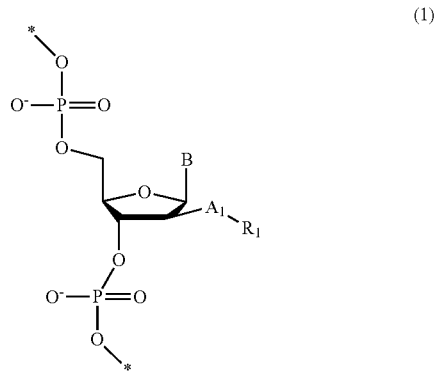

where $A_1$ represents —S—, —S—S—, or —Se—, B represents a base, $R_1$ represents a decomposable protecting group, and a symbol * represents a bond to a sugar of an adjacent nucleotide, and a reverse primer being complementary to a part of a sequence of a sense strand of the template DNA and having the structure represented by formula (1);

an amplification step of performing a plurality of cycles of polymerase chain reaction (PCR) by using the template DNA as a template to form a forward-side extended chain being the forward primer extended and a reverse-side extended chain being the reverse primer extended, and of annealing the forward-side extended chain and the reverse-side extended chain to form double-stranded DNA with 3'-recessed ends;

blunting step of making the 3' ends of the double-stranded DNA blunt by Klenow fragment; and a deprotection cleavage step of deprotecting the $R_1$, and cleaving DNA at the bond at the 3'-carbon of formula (1) to form a sticky end with a 3'-protruding end.

6. The method according to claim 5, wherein
the $R_1$ is a photodecomposable protecting group represented by the following formula (2A):

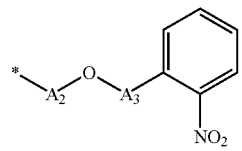

where $A_2$ represents an alkylene group having 1 to 3 carbon atoms, $A_3$ represents an alkylene group having 1 to 3 carbon atoms, and a symbol * represents a bond to $A_1$, and is deprotected by photoirradiation in the deprotection cleavage step.

7. The method according to claim 5, wherein
the $R_1$ is a fluoride decomposable protecting group represented by the following formula (2B)

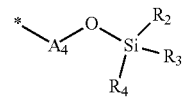

where $A_4$ represents an alkylene group having 1 to 3 carbon atoms, $R_2$ to $R_4$ each represent a straight or branched alkyl group having 1 to 4 carbon atoms, the $R_2$ to $R_4$ may be the same as or different from each other, and a symbol * represents a bond to $A_1$, and is deprotected by a fluoride in the deprotection cleavage step.

8. The method according to claim 6, wherein
the $R_1$ is a 2-nitrobenzyloxymethyl group represented by the following formula (3A):

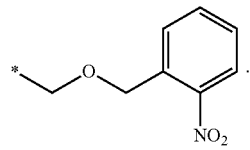

9. The method according to claim 7, wherein
the $R_1$ is a triisopropylsilyloxymethyl group represented by the following formula (3B):

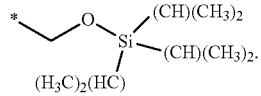

10. The device according to claim 4, wherein
the $R_1$ is a photodecomposable protecting group represented by the following formula (2A):

(2A)

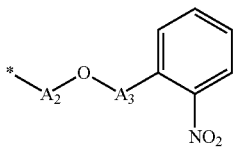

where $A_2$ represents an alkylene group having 1 to 3 carbon atoms, $A_3$ represents an alkylene group having 1 to 3 carbon atoms, and a symbol * represents a bond to $A_1$, and is deprotected by photoirradiation in the deprotection cleavage step.

11. The device according to claim 4, wherein the $R_1$ is a fluoride decomposable protecting group represented by the following formula (2B):

(2B)

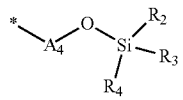

where $A_4$ represents an alkylene group having 1 to 3 carbon atoms, $R_2$ to $R_4$ each represent a straight or branched alkyl group having 1 to 4 carbon atoms, the $R_2$ to $R_4$ may be the same as or different from each other, and a symbol * represents a bond to $A_1$, and is deprotected by a fluoride in the deprotection cleavage step.

12. The device according to claim 10, wherein the $R_1$ is a 2-nitrobenzyloxymethyl group represented by the following formula (3A):

(3A)

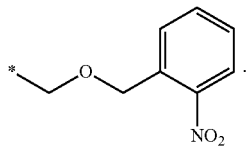

13. The device according to claim 11, wherein the $R_1$ is a triisopropylsilyloxymethyl group represented by the following formula (3B):

(3B)

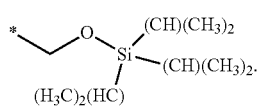

* * * * *

UNITED STATES PATENT AND TRADEMARK OFFICE
CERTIFICATE OF CORRECTION

| | | |
|---|---|---|
| PATENT NO. | : 12,359,254 B2 | Page 1 of 1 |
| APPLICATION NO. | : 17/631418 | |
| DATED | : July 15, 2025 | |
| INVENTOR(S) | : Hiroshi Abe | |

It is certified that error appears in the above-identified patent and that said Letters Patent is hereby corrected as shown below:

On the Title Page

Column 2, item (57) Abstract, Line 1, above formula (1), insert:
-- A primer for amplifying a nucleic acid having a structure represented by formula (1): --

Signed and Sealed this
Sixteenth Day of September, 2025

Coke Morgan Stewart
*Acting Director of the United States Patent and Trademark Office*